(12) United States Patent
Urbanski et al.

(10) Patent No.: US 11,801,087 B2
(45) Date of Patent: Oct. 31, 2023

(54) APPARATUS AND METHODS FOR PUNCTURING TISSUE

(71) Applicant: Boston Scientific Medical Device Limited, Galway (IE)

(72) Inventors: John Paul Urbanski, Toronto (CA); Brock Miller, Toronto (CA); Matthew Gravett, Milton (CA); Rund Abou-Marie, Mississauga (CA); Kai-Lon Fok, Mississauga (CA); Maria Luk, Kleinburg (CA); Ahmad Kamal, Milton (CA)

(73) Assignee: Boston Scientific Medical Device Limited, Galway (IE)

( * ) Notice: Subject to any disclaimer, the term of this patent is extended or adjusted under 35 U.S.C. 154(b) by 301 days.

(21) Appl. No.: 17/095,984

(22) Filed: Nov. 12, 2020

(65) Prior Publication Data

US 2021/0137584 A1 May 13, 2021

Related U.S. Application Data

(60) Provisional application No. 62/934,830, filed on Nov. 13, 2019.

(51) Int. Cl.
*A61B 18/14* (2006.01)
*A61B 18/00* (2006.01)
*A61B 90/00* (2016.01)

(52) U.S. Cl.
CPC ............ *A61B 18/1477* (2013.01); *A61B 2018/00136* (2013.01); *A61B 2018/00363* (2013.01);

(Continued)

(58) Field of Classification Search
CPC ............ A61B 18/1477; A61B 18/1492; A61B 2018/00136; A61B 2018/00363; A61B 2018/00577; A61B 2018/00839; A61B 2018/144; A61B 2090/065; A61B 2090/376; A61B 2090/3925; A61B 2090/3966; A61B 2090/3995; A61B 5/065; A61B 5/318; A61B 5/6851; A61B 5/6869; A61B 5/6885; A61M 25/005;
(Continued)

(56) References Cited

U.S. PATENT DOCUMENTS 175,254 A 3/1876 Oberly
827,626 A 7/1906 Gillet
(Continued)

*Primary Examiner* — Michael F Peffley
(74) *Attorney, Agent, or Firm* — Nelson Mullins; Riley & Scarborough

(57) ABSTRACT

Methods and apparatus are disclosed for puncturing tissue, including a surgical introducer with a stiff main body and a flexible tip which can be used with a puncture device to gain epicardial access. The surgical introducer comprises an introducer shaft having a rigid portion and a flexible tip portion. The rigid portion has a metal tube extending to the rigid portion distal end. The flexible tip portion is distal of the metal tube distal end. The flexible tip portion includes a first polymer and a second polymer, wherein the second polymer is more flexible than the first polymer. The second polymer extends distally from the metal tube distal end to define a second polymer flexible tip segment. The first polymer extends distally from the second polymer flexible tip segment end to define a flexible tip portion cap.

20 Claims, 31 Drawing Sheets

(52) U.S. Cl.
CPC .............. *A61B 2018/00577* (2013.01); *A61B 2018/00839* (2013.01); *A61B 2018/144* (2013.01); *A61B 2090/3966* (2016.02)

(58) Field of Classification Search
CPC .......... A61M 25/0053; A61M 25/0054; A61M 25/008; A61M 2025/09133; A61M 2025/0915; A61M 2025/09175
See application file for complete search history.

(56) References Cited

U.S. PATENT DOCUMENTS

| | | | |
|---|---|---|---|
| 848,711 A | 4/1907 | Weaver | |
| 1,072,954 A | 9/1913 | Junn | |
| 1,279,654 A | 9/1918 | Charlesworth | |
| 1,918,094 A | 7/1933 | Geekas | |
| 1,996,986 A | 4/1935 | Weinberg | |
| 2,021,989 A | 11/1935 | De Master | |
| 2,146,636 A | 2/1939 | Ipchow | |
| 3,429,574 A | 2/1969 | Williams | |
| 3,448,739 A | 6/1969 | Stark et al. | |
| 3,575,415 A | 4/1971 | Fulp et al. | |
| 3,595,239 A | 7/1971 | Petersen | |
| 4,129,129 A | 12/1978 | Amrine | |
| 4,244,362 A | 1/1981 | Anderson | |
| 4,401,124 A | 8/1983 | Guess et al. | |
| 4,639,252 A | 1/1987 | Kelly et al. | |
| 4,641,649 A | 2/1987 | Walinsky et al. | |
| 4,669,467 A | 6/1987 | Willett et al. | |
| 4,682,596 A | 7/1987 | Bales et al. | |
| 4,690,175 A * | 9/1987 | Ouchi ................ | A61B 1/0055 138/131 |
| 4,790,311 A | 12/1988 | Ruiz | |
| 4,790,809 A | 12/1988 | Kuntz | |
| 4,793,350 A | 12/1988 | Mar et al. | |
| 4,807,620 A | 2/1989 | Strul et al. | |
| 4,832,048 A * | 5/1989 | Cohen ................ | A61B 18/1492 606/41 |
| 4,840,622 A | 6/1989 | Hardy | |
| 4,863,441 A | 9/1989 | Lindsay et al. | |
| 4,884,567 A | 12/1989 | Elliott et al. | |
| 4,892,104 A | 1/1990 | Ito et al. | |
| 4,896,671 A | 1/1990 | Cunningham et al. | |
| 4,928,693 A | 5/1990 | Goodin et al. | |
| 4,936,281 A | 6/1990 | Stasz | |
| 4,960,410 A | 10/1990 | Pinchuk | |
| 4,977,897 A | 12/1990 | Hurwitz | |
| 4,998,933 A | 3/1991 | Eggers et al. | |
| 5,006,119 A | 4/1991 | Acker et al. | |
| 5,019,076 A | 5/1991 | Yamanashi et al. | |
| 5,047,026 A | 9/1991 | Rydell | |
| 5,081,997 A | 1/1992 | Bosley et al. | |
| 5,098,431 A | 3/1992 | Rydell | |
| 5,112,048 A | 5/1992 | Kienle | |
| 5,154,724 A | 10/1992 | Andrews | |
| 5,201,756 A | 4/1993 | Horzewski et al. | |
| 5,209,741 A | 5/1993 | Spaeth | |
| 5,211,183 A | 5/1993 | Wilson | |
| 5,221,256 A | 6/1993 | Mahurkar | |
| 5,230,349 A | 7/1993 | Langberg | |
| 5,281,216 A | 1/1994 | Klicek | |
| 5,300,068 A | 4/1994 | Rosar et al. | |
| 5,300,069 A | 4/1994 | Hunsberger et al. | |
| 5,308,342 A * | 5/1994 | Sepetka ............ | A61M 25/0054 604/525 |
| 5,314,418 A | 5/1994 | Takano et al. | |
| 5,318,525 A | 6/1994 | West et al. | |
| 5,327,905 A | 7/1994 | Avitall | |
| 5,364,393 A | 11/1994 | Auth et al. | |
| 5,372,596 A | 12/1994 | Klicek et al. | |
| 5,380,304 A | 1/1995 | Parker | |
| 5,397,304 A | 3/1995 | Truckai | |
| 5,403,338 A | 4/1995 | Milo | |
| 5,423,809 A | 6/1995 | Klicek | |
| 5,425,382 A | 6/1995 | Golden et al. | |
| 5,490,859 A | 2/1996 | Mische et al. | |
| 5,497,774 A | 3/1996 | Swartz et al. | |
| 5,507,751 A | 4/1996 | Goode et al. | |
| 5,509,411 A | 4/1996 | Littmann et al. | |
| 5,540,681 A | 7/1996 | Strul et al. | |
| 5,545,200 A | 8/1996 | West et al. | |
| 5,555,618 A | 9/1996 | Winkler | |
| 5,571,088 A | 11/1996 | Lennox et al. | |
| 5,575,766 A | 11/1996 | Swartz et al. | |
| 5,575,772 A | 11/1996 | Lennox | |
| 5,599,347 A | 2/1997 | Hart et al. | |
| 5,605,162 A | 2/1997 | Mirzaee et al. | |
| 5,617,878 A | 4/1997 | Taheri | |
| 5,622,169 A | 4/1997 | Golden et al. | |
| 5,624,430 A | 4/1997 | Eton et al. | |
| 5,658,263 A * | 8/1997 | Dang ................ | A61M 25/0041 604/525 |
| 5,667,488 A | 9/1997 | Lundquist et al. | |
| 5,673,695 A | 10/1997 | McGee et al. | |
| 5,674,208 A | 10/1997 | Berg et al. | |
| 5,683,366 A | 11/1997 | Eggers et al. | |
| 5,720,744 A | 2/1998 | Eggleston et al. | |
| 5,741,249 A | 4/1998 | Moss et al. | |
| 5,766,135 A | 6/1998 | Terwilliger | |
| 5,779,688 A | 7/1998 | Imran et al. | |
| 5,810,764 A | 9/1998 | Eggers et al. | |
| 5,814,028 A | 9/1998 | Swartz et al. | |
| 5,830,214 A | 11/1998 | Flom et al. | |
| 5,836,875 A | 11/1998 | Webster, Jr. | |
| 5,849,011 A | 12/1998 | Jones et al. | |
| 5,851,210 A | 12/1998 | Torossian | |
| 5,885,227 A | 3/1999 | Finlayson | |
| 5,888,201 A | 3/1999 | Stinson et al. | |
| 5,893,848 A | 4/1999 | Negus et al. | |
| 5,893,885 A | 4/1999 | Webster, Jr. | |
| 5,904,679 A | 5/1999 | Clayman | |
| 5,916,210 A | 6/1999 | Winston | |
| 5,921,957 A | 7/1999 | Killion et al. | |
| 5,931,818 A | 8/1999 | Werp et al. | |
| 5,944,023 A | 8/1999 | Johnson et al. | |
| 5,951,482 A | 9/1999 | Winston et al. | |
| 5,957,842 A | 9/1999 | Littmann et al. | |
| 5,964,757 A | 10/1999 | Ponzi | |
| 5,967,976 A | 10/1999 | Larsen et al. | |
| 5,989,276 A | 11/1999 | Houser et al. | |
| 6,007,555 A | 12/1999 | Devine | |
| 6,009,877 A | 1/2000 | Edwards | |
| 6,013,072 A | 1/2000 | Winston et al. | |
| 6,017,340 A | 1/2000 | Cassidy et al. | |
| 6,018,676 A | 1/2000 | Davis et al. | |
| 6,030,380 A | 2/2000 | Auth et al. | |
| 6,032,674 A | 3/2000 | Eggers et al. | |
| 6,048,349 A | 4/2000 | Winston et al. | |
| 6,053,870 A | 4/2000 | Fulton, III | |
| 6,053,904 A | 4/2000 | Scribner et al. | |
| 6,056,747 A | 5/2000 | Saadat et al. | |
| 6,063,093 A | 5/2000 | Winston et al. | |
| 6,093,185 A | 7/2000 | Ellis et al. | |
| 6,106,515 A | 8/2000 | Winston et al. | |
| 6,106,520 A | 8/2000 | Laufer et al. | |
| 6,117,131 A | 9/2000 | Taylor | |
| 6,142,992 A | 11/2000 | Cheng et al. | |
| 6,146,380 A | 11/2000 | Racz et al. | |
| 6,155,264 A | 12/2000 | Ressemann et al. | |
| 6,156,031 A | 12/2000 | Aita et al. | |
| 6,171,305 B1 | 1/2001 | Sherman | |
| 6,179,824 B1 | 1/2001 | Eggers et al. | |
| 6,193,676 B1 | 2/2001 | Winston et al. | |
| 6,193,715 B1 | 2/2001 | Wrublewski et al. | |
| 6,210,408 B1 | 4/2001 | Chandrasekaran et al. | |
| 6,217,575 B1 | 4/2001 | Devore et al. | |
| 6,221,061 B1 | 4/2001 | Engelson et al. | |
| 6,228,076 B1 | 5/2001 | Winston et al. | |
| 6,245,054 B1 | 6/2001 | Fuimaono et al. | |
| 6,267,758 B1 | 7/2001 | Daw et al. | |
| 6,283,983 B1 | 9/2001 | Makower et al. | |
| 6,292,678 B1 | 9/2001 | Hall et al. | |
| 6,293,945 B1 | 9/2001 | Parins et al. | |
| 6,296,615 B1 | 10/2001 | Brockway et al. | |

(56) References Cited

U.S. PATENT DOCUMENTS

| | | |
|---|---|---|
| 6,296,636 B1 | 10/2001 | Cheng et al. |
| 6,302,898 B1 | 10/2001 | Edwards et al. |
| 6,304,769 B1 | 10/2001 | Arenson et al. |
| 6,315,777 B1 | 11/2001 | Comben |
| 6,328,699 B1 | 12/2001 | Eigler et al. |
| 6,360,128 B2 | 3/2002 | Kordis et al. |
| 6,364,877 B1 | 4/2002 | Goble et al. |
| 6,385,472 B1 | 5/2002 | Hall et al. |
| 6,394,976 B1 | 5/2002 | Winston et al. |
| 6,395,002 B1 | 5/2002 | Ellman et al. |
| 6,398,791 B1 * | 6/2002 | Que .................. A61B 17/221 606/127 |
| 6,419,674 B1 | 7/2002 | Bowser et al. |
| 6,428,551 B1 | 8/2002 | Hall et al. |
| 6,450,989 B2 | 9/2002 | Dubrul et al. |
| 6,475,214 B1 | 11/2002 | Moaddeb |
| 6,485,485 B1 | 11/2002 | Winston et al. |
| 6,508,754 B1 | 1/2003 | Liprie et al. |
| 6,524,303 B1 | 2/2003 | Garibaldi |
| 6,530,923 B1 | 3/2003 | Dubrul et al. |
| 6,554,827 B2 | 4/2003 | Chandrasekaran et al. |
| 6,562,031 B2 | 5/2003 | Chandrasekaran et al. |
| 6,562,049 B1 | 5/2003 | Norlander et al. |
| 6,565,562 B1 | 5/2003 | Shah et al. |
| 6,607,529 B1 | 8/2003 | Jones et al. |
| 6,632,222 B1 | 10/2003 | Edwards et al. |
| 6,639,999 B1 | 10/2003 | Cookingham et al. |
| 6,650,923 B1 | 11/2003 | Lesh et al. |
| 6,651,672 B2 | 11/2003 | Roth |
| 6,652,508 B2 * | 11/2003 | Griffin .............. A61M 25/0045 604/524 |
| 6,662,034 B2 | 12/2003 | Segner et al. |
| 6,663,621 B1 | 12/2003 | Winston et al. |
| 6,702,811 B2 | 3/2004 | Stewart et al. |
| 6,709,444 B1 | 3/2004 | Makower |
| 6,723,052 B2 | 4/2004 | Mills |
| 6,733,511 B2 | 5/2004 | Hall et al. |
| 6,740,103 B2 | 5/2004 | Hall et al. |
| 6,752,800 B1 | 6/2004 | Winston et al. |
| 6,755,816 B2 | 6/2004 | Ritter et al. |
| 6,811,544 B2 | 11/2004 | Schaer |
| 6,814,733 B2 | 11/2004 | Schwartz et al. |
| 6,820,614 B2 | 11/2004 | Bonutti |
| 6,834,201 B2 | 12/2004 | Gillies et al. |
| 6,842,639 B1 | 1/2005 | Winston et al. |
| 6,852,109 B2 | 2/2005 | Winston et al. |
| 6,855,143 B2 | 2/2005 | Davison et al. |
| 6,860,856 B2 | 3/2005 | Ward et al. |
| 6,869,431 B2 | 3/2005 | Maguire et al. |
| 6,911,026 B1 | 6/2005 | Hall et al. |
| 6,951,554 B2 | 10/2005 | Johansen et al. |
| 6,951,555 B1 | 10/2005 | Suresh et al. |
| 6,955,675 B2 | 10/2005 | Jain |
| 6,970,732 B2 | 11/2005 | Winston et al. |
| 6,980,843 B2 | 12/2005 | Eng et al. |
| 7,029,470 B2 | 4/2006 | Francischelli et al. |
| 7,056,294 B2 | 6/2006 | Khairkhahan et al. |
| 7,083,566 B2 | 8/2006 | Tornes et al. |
| 7,112,197 B2 | 9/2006 | Hartley et al. |
| 7,335,197 B2 | 2/2008 | Sage et al. |
| 7,618,430 B2 | 11/2009 | Scheib |
| 7,651,492 B2 | 1/2010 | Wham |
| 7,666,203 B2 | 2/2010 | Chanduszko et al. |
| 7,678,081 B2 | 3/2010 | Whiting et al. |
| 7,682,360 B2 | 3/2010 | Guerra |
| 7,828,796 B2 | 11/2010 | Wong et al. |
| 7,900,928 B2 | 3/2011 | Held et al. |
| 8,192,425 B2 | 6/2012 | Mirza et al. |
| 8,257,323 B2 | 9/2012 | Joseph et al. |
| 8,388,549 B2 | 3/2013 | Paul et al. |
| 8,500,697 B2 | 8/2013 | Kurth et al. |
| 9,216,056 B2 * | 12/2015 | Datta ................ A61B 18/1492 |
| 11,339,579 B1 | 5/2022 | Stearns |
| 2001/0012934 A1 | 8/2001 | Chandrasekaran et al. |
| 2001/0021867 A1 | 9/2001 | Kordis et al. |
| 2002/0019644 A1 | 2/2002 | Hastings et al. |
| 2002/0022781 A1 | 2/2002 | McIntire et al. |
| 2002/0022836 A1 | 2/2002 | Goble et al. |
| 2002/0035361 A1 | 3/2002 | Houser et al. |
| 2002/0087153 A1 | 7/2002 | Roschak et al. |
| 2002/0087156 A1 | 7/2002 | Maguire et al. |
| 2002/0111618 A1 | 8/2002 | Stewart et al. |
| 2002/0123749 A1 | 9/2002 | Jain |
| 2002/0147485 A1 | 10/2002 | Mamo et al. |
| 2002/0169377 A1 | 11/2002 | Khairkhahan et al. |
| 2002/0188302 A1 | 12/2002 | Berg et al. |
| 2002/0198521 A1 | 12/2002 | Maguire |
| 2003/0032929 A1 | 2/2003 | McGuckin |
| 2003/0040742 A1 | 2/2003 | Underwood et al. |
| 2003/0144658 A1 | 7/2003 | Schwartz et al. |
| 2003/0158480 A1 | 8/2003 | Tornes et al. |
| 2003/0163153 A1 | 8/2003 | Scheib |
| 2003/0225392 A1 | 12/2003 | McMichael et al. |
| 2004/0015162 A1 | 1/2004 | McGaffigan |
| 2004/0024396 A1 | 2/2004 | Eggers |
| 2004/0030328 A1 | 2/2004 | Eggers et al. |
| 2004/0044350 A1 | 3/2004 | Martin et al. |
| 2004/0073243 A1 | 4/2004 | Sepetka et al. |
| 2004/0077948 A1 | 4/2004 | Violante et al. |
| 2004/0116851 A1 | 6/2004 | Johansen et al. |
| 2004/0127963 A1 | 7/2004 | Uchida et al. |
| 2004/0133113 A1 | 7/2004 | Krishnan |
| 2004/0133130 A1 | 7/2004 | Ferry et al. |
| 2004/0143256 A1 | 7/2004 | Bednarek |
| 2004/0147950 A1 | 7/2004 | Mueller et al. |
| 2004/0181213 A1 | 9/2004 | Gondo |
| 2004/0230188 A1 | 11/2004 | Cioanta et al. |
| 2005/0004585 A1 | 1/2005 | Hall et al. |
| 2005/0010208 A1 | 1/2005 | Winston et al. |
| 2005/0049628 A1 | 3/2005 | Schweikert et al. |
| 2005/0059966 A1 | 3/2005 | McClurken et al. |
| 2005/0065507 A1 | 3/2005 | Hartley et al. |
| 2005/0085806 A1 | 4/2005 | Auge et al. |
| 2005/0096529 A1 | 5/2005 | Cooper et al. |
| 2005/0101984 A1 | 5/2005 | Chanduszko et al. |
| 2005/0119556 A1 | 6/2005 | Gillies et al. |
| 2005/0137527 A1 | 6/2005 | Kunin |
| 2005/0149012 A1 | 7/2005 | Penny et al. |
| 2005/0203504 A1 | 9/2005 | Wham et al. |
| 2005/0203507 A1 | 9/2005 | Truckai et al. |
| 2005/0261607 A1 | 11/2005 | Johansen et al. |
| 2005/0288631 A1 | 12/2005 | Lewis et al. |
| 2006/0041253 A1 | 2/2006 | Newton et al. |
| 2006/0074398 A1 | 4/2006 | Whiting et al. |
| 2006/0079769 A1 | 4/2006 | Whiting et al. |
| 2006/0079787 A1 | 4/2006 | Whiting et al. |
| 2006/0079884 A1 | 4/2006 | Manzo et al. |
| 2006/0085054 A1 | 4/2006 | Zikorus et al. |
| 2006/0089638 A1 | 4/2006 | Carmel et al. |
| 2006/0106375 A1 | 5/2006 | Werneth et al. |
| 2006/0135962 A1 | 6/2006 | Kick et al. |
| 2006/0142756 A1 | 6/2006 | Davies et al. |
| 2006/0189972 A1 | 8/2006 | Grossman |
| 2006/0241586 A1 | 10/2006 | Wilk |
| 2006/0247672 A1 | 11/2006 | Vidlund et al. |
| 2006/0264927 A1 | 11/2006 | Ryan |
| 2006/0276710 A1 | 12/2006 | Krishnan |
| 2007/0060879 A1 | 3/2007 | Weitzner et al. |
| 2007/0066975 A1 | 3/2007 | Wong et al. |
| 2007/0118099 A1 | 5/2007 | Trout |
| 2007/0123964 A1 | 5/2007 | Davies et al. |
| 2007/0167775 A1 | 7/2007 | Kochavi et al. |
| 2007/0208256 A1 | 9/2007 | Marilla |
| 2007/0225681 A1 | 9/2007 | House |
| 2007/0270791 A1 | 11/2007 | Wang et al. |
| 2008/0039865 A1 | 2/2008 | Shaher et al. |
| 2008/0042360 A1 | 2/2008 | Veikley |
| 2008/0086120 A1 | 4/2008 | Mirza et al. |
| 2008/0097213 A1 | 4/2008 | Carlson et al. |
| 2008/0108987 A1 | 5/2008 | Bruszewski et al. |
| 2008/0146918 A1 | 6/2008 | Magnin et al. |
| 2008/0171934 A1 | 7/2008 | Greenan et al. |
| 2008/0208121 A1 | 8/2008 | Youssef et al. |
| 2008/0275439 A1 | 11/2008 | Francischelli et al. |

(56) References Cited

U.S. PATENT DOCUMENTS

| | | |
|---|---|---|
| 2009/0105742 A1 | 4/2009 | Kurth et al. |
| 2009/0138009 A1 | 5/2009 | Viswanathan et al. |
| 2009/0163850 A1 | 6/2009 | Betts et al. |
| 2009/0177114 A1 | 7/2009 | Chin et al. |
| 2009/0264977 A1 | 10/2009 | Bruszewski et al. |
| 2010/0087789 A1 | 4/2010 | Leeflang et al. |
| 2010/0125282 A1 | 5/2010 | Machek et al. |
| 2010/0168684 A1 | 7/2010 | Ryan |
| 2010/0179632 A1 | 7/2010 | Bruszewski et al. |
| 2010/0191142 A1 | 7/2010 | Paul et al. |
| 2010/0194047 A1 | 8/2010 | Sauerwine |
| 2011/0046619 A1 | 2/2011 | Ducharme |
| 2011/0152716 A1 | 6/2011 | Chudzik et al. |
| 2011/0160592 A1 | 6/2011 | Mitchell |
| 2011/0190763 A1 | 8/2011 | Urban et al. |
| 2012/0232546 A1 | 9/2012 | Mirza et al. |
| 2012/0265055 A1 | 10/2012 | Melsheimer et al. |
| 2012/0330156 A1 | 12/2012 | Brown et al. |
| 2013/0184551 A1 | 7/2013 | Paganelli et al. |
| 2013/0184735 A1 | 7/2013 | Fischell et al. |
| 2013/0282084 A1 | 10/2013 | Mathur et al. |
| 2014/0206987 A1 | 7/2014 | Urbanski et al. |
| 2014/0296769 A1 | 10/2014 | Hyde et al. |
| 2016/0220741 A1 | 8/2016 | Garrison et al. |
| 2019/0021763 A1 | 1/2019 | Zhou et al. |
| 2019/0247035 A1 | 8/2019 | Gittard et al. |

\* cited by examiner

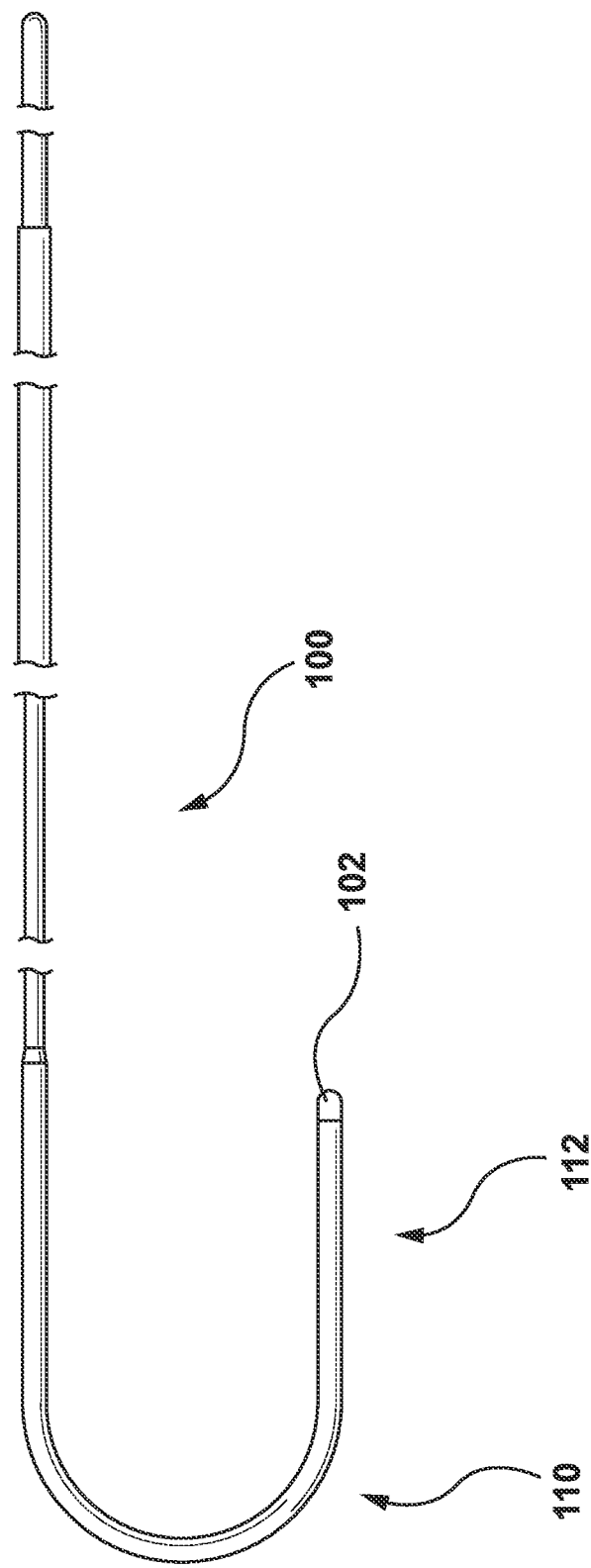

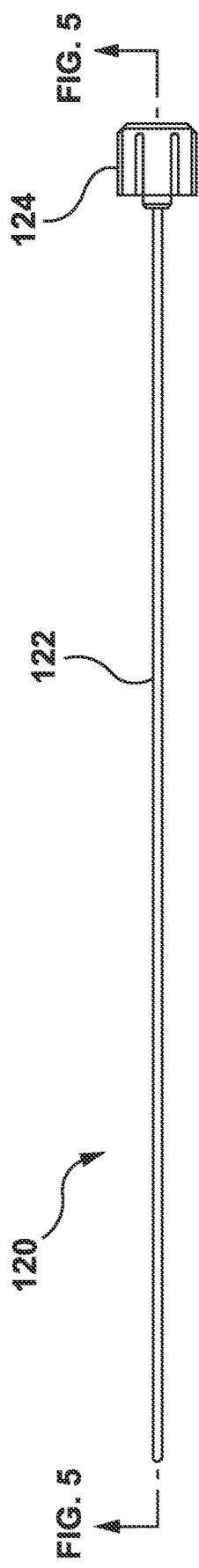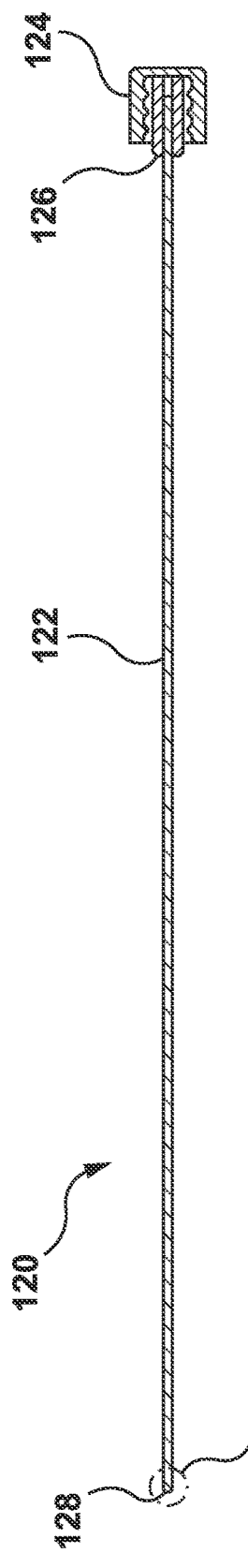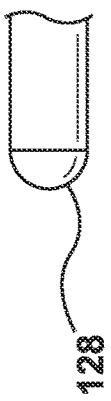
FIG. 4
FIG. 5
FIG. 6

APPARATUS AND METHODS FOR PUNCTURING TISSUE

TECHNICAL FIELD

The disclosure relates to systems and methods of delivering energy to tissue. More specifically, it relates to delivering energy using electrosurgical devices to puncture tissue.

SUMMARY

The safety of a procedure for puncturing a target tissue with a puncture device can be increased using a method of confirming the position of the tip of the puncture device relative to the target tissue. The method uses an elongate device (e.g. a radiofrequency (RF) guidewire) having a tip electrode, which is configured for collecting electrograms (EGMs) and for delivering electrical energy for puncturing the tissue, and the method including collecting EGMs to indirectly measure and monitor the pressure applied against the target tissue by the elongate device to thereby indicate tip location with respect to the target tissue. In some embodiments the target tissue is on a pericardium and the method includes collecting epicardial electrograms (EGMs) to measure and monitor the pressure applied against the pericardial target tissue site. In other embodiments, the tissue is some part of a body other than a pericardium, for example, a septum of a heart.

In embodiments in which the target tissue is on a pericardium, a stiff introducer is typically used to provide access to the pericardium for the puncture device. The introducer being stiff allows the physician to control the advancement of the introducer. There are some risks associated with advancing a stiff introducer towards the outer surface of a heart including inadvertent laceration to the heart surface or puncture of the heart wall. The problem of inadvertent damage to the outside of a heart by an introducer when gaining epicardial access can be addressed by an introducer with a stiff main body and a flexible tip.

In a first broad aspect, embodiments of the present invention include an introducer for use with an elongate puncture device, with the surgical introducer comprising an introducer shaft having a rigid portion and a flexible tip portion. The rigid portion has a rigid portion distal end, and a metal tube extending to the rigid portion distal end. The metal tube has a metal tube distal end. The flexible tip portion is distal of the metal tube distal end, with the flexible tip portion including a first polymer and a second polymer, and the second polymer being more flexible than the first polymer. The second polymer extends distally from the metal tube distal end to define a second polymer flexible tip segment having a second polymer flexible tip segment end. The first polymer extends distally from the second polymer flexible tip segment end to define a flexible tip portion cap. The rigid portion and the flexible tip portion define a lumen, and the flexible tip portion cap defines a distal end opening which is in fluid communication with the lumen.

In typical embodiments of the first broad aspect, the distal end opening is forward facing, and the surgical introducer includes an outside layer of a polymer on an outside of the metal tube. Typical embodiments have an inside layer of polymer on an inside of the metal tube for at least a distal portion of the metal tube. Embodiments of the first broad aspect typically include the second polymer flexible tip segment having a second polymer flexible tip segment length of length L2 and the flexible tip portion cap having a flexible tip portion cap length of length L1, and the length L2 being greater than length L1.

In some embodiments, the flexible tip portion has a length of about 1 to 3 cm. In some other embodiments, the flexible tip portion has a length of 2 to 3 cm. In some embodiments, the first polymer comprises a HDPE and the second polymer comprises a LDPE. In typical embodiments, the metal tube comprises a steel, and in particular embodiments, the metal tube is stainless steel.

In some embodiments of the first broad aspect, the second polymer extends proximally from the metal tube distal end on an outside of the metal tube. In some such embodiments, the second polymer extends proximally from the metal tube distal end on the outside of the metal tube to define a second polymer outside layer which has a second polymer outside layer proximal end, and the first polymer extends proximally from the second polymer outside layer proximal end on the outside of the metal tube to define a first polymer outside layer. In other such embodiments, the second polymer flexible tip segment has a second polymer flexible tip segment length of length L2 and the second polymer extends proximally from the metal tube distal end on the outside of the metal tube to define a second polymer outside layer which extends longitudinally and proximally from the metal tube distal end for a distance less than length L2. In some examples, the rigid portion has a rigid portion proximal end and the second polymer outside layer extends proximally to the rigid portion proximal end.

Some embodiments of the first broad aspect comprise the second polymer extending proximally from the metal tube distal end on the inside of the metal tube to define a second polymer inside layer having a second polymer inside layer proximal end. In some such embodiments, the rigid portion has a rigid portion proximal end and the second polymer inside layer proximal end is distal of the rigid portion proximal end. In some examples, a diameter of the lumen proximal of the second polymer inside layer is greater than the diameter of the lumen defined by the flexible tip portion.

Some embodiments of the first broad aspect include the first polymer extending proximally from the flexible tip portion cap to form a first polymer inside layer, with the first polymer inside layer defining at least a portion of the lumen. In some such embodiments, the rigid portion has a rigid portion proximal end and the first polymer inside layer extends proximally to the rigid portion proximal end. In some examples, a diameter of the lumen which is defined by the rigid portion is substantially equal to the diameter of the lumen which is defined by the flexible tip portion.

BRIEF DESCRIPTION OF THE DRAWINGS

In order that the invention may be readily understood, embodiments of the invention are illustrated by way of examples in the accompanying drawings, in which:

FIG. 1 is an illustration of a radiofrequency (RF) guidewire in accordance with an embodiment of the present invention;

FIG. 4 is an illustration of a stylet in accordance with an embodiment of the present invention;

FIG. 5 is a cross sectional view of the embodiment of FIG. 4;

FIG. 6 is an illustration of detail A of FIG. 4;

FIG. 20-1, and FIG. 20A to FIG. 20F illustrate a method in accordance with an embodiment of the present invention;

DETAILED DESCRIPTION

Figure 2:
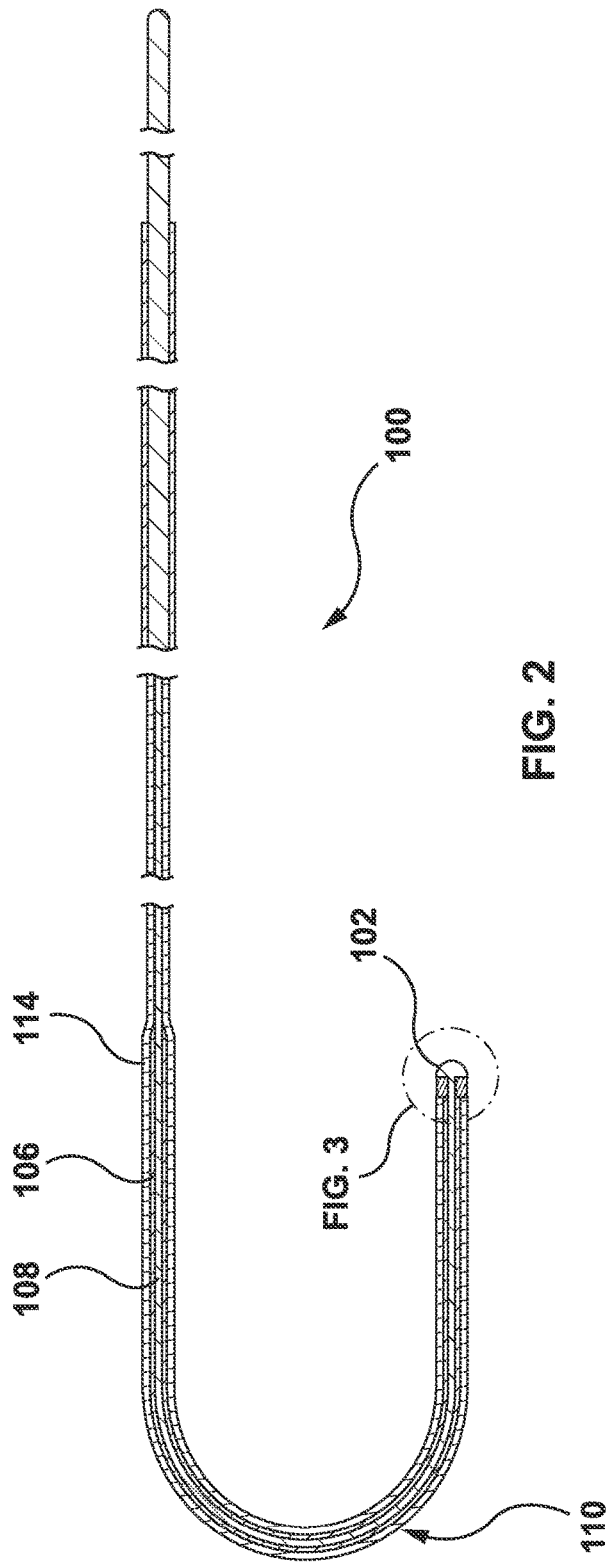
FIG. 2 is a cross sectional view of the embodiment of FIG. 1.

Minimally invasive catheterization of the pericardial space is required for diagnostic procedures and treatment of a variety of arrhythmias. Although epicardial ablation is a preferred route in many situations (for ventricular tachycardias, for instance), physicians may resort to common endocardial ablation due to uncertainties involved in access and high clinical complication rate. The current standard procedure for epicardial access is facilitated by using a 17 Ga Tuohy needle that percutaneously punctures the pericardial sac via the subxiphoid or parasternal intercostal or apical approach. This puncture is typically performed under fluoroscopic guidance using a combination of anterior-posterior and lateral views. Radiopaque contrast agents are periodically injected to provide positive feedback to the user on tip position, and whether the needle tip has successfully broached the pericardial sack. With this approach there is the possibility of lacerating the epicardium, cardiac vessels or surrounding soft tissue structures. There is also the risk of inadvertent entry into the ventricle that can lead to an effusion and perhaps tamponade. Any new devices or methods to improve the safety and predictability to confirm targeted tissue site and reduce chance of complications would be beneficial.

The inventors have come up with a unique and heretofore undiscovered solution of improving the safety of a procedure for puncturing a target tissue with a puncture device, which includes using a method of confirming the position of the tip of the puncture device relative to the target tissue. The method uses an elongate device (e.g. a radiofrequency (RF) guidewire) having a tip electrode which is configured for collecting local electrograms (EGMs) and for delivering energy for puncturing the tissue, with the method including collecting EGMs to indicate tip location with respect to the target tissue. The elongate device doesn't specifically measure the EGM but passes on the signal to EGM signal processing equipment. In some embodiments the target tissue is on a pericardium and the method includes collecting local epicardial electrograms (EGMs) to indirectly measure and monitor the pressure applied against the pericardial target tissue site. In other embodiments, the tissue is a septum of a heart and the method includes collecting intracardiac electrograms (EGMs) to indirectly measure and monitor the pressure applied against the septum. Typical embodiments include collecting an EGM signal during tenting of the target tissue.

One embodiment is for a guidewire that is operable to provide tip information back to the user on confirming location of the tip of the device in reference to the targeted tissue. The invention uses local epicardial electrograms (EGM) to aid in confirming location of the guidewire tip when approaching the heart, docking with the targeted tissue before puncturing and after puncturing the sac.

In embodiments in which the target tissue is on a pericardium, a stiff introducer is typically used to provide access to the pericardium for the puncture device. The introducer being stiff allows the physician to control the advancement of the introducer. There are some risks associated with advancing a stiff introducer towards the outer surface of a heart including inadvertent laceration to the heart surface or puncture of the heart wall. The problem of inadvertent damage to the outside of a heart by an introducer when gaining epicardial access can be solved by an introducer with a stiff main body and a flexible tip.

Furthermore, the challenge of safely gaining epicardial access can be addressed by a method using (1) an elongate device (e.g. a RF GW) having a tip electrode which is configured for collecting EGMs and for delivering energy for puncturing tissue, and (2) an introducer with a stiff main body and flexible tip which allows a tangential approach to the heart.

With specific reference now to the drawings in detail, it is stressed that the particulars shown are by way of example and for purposes of illustrative discussion of certain embodiments of the present invention only. Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Figure 13:
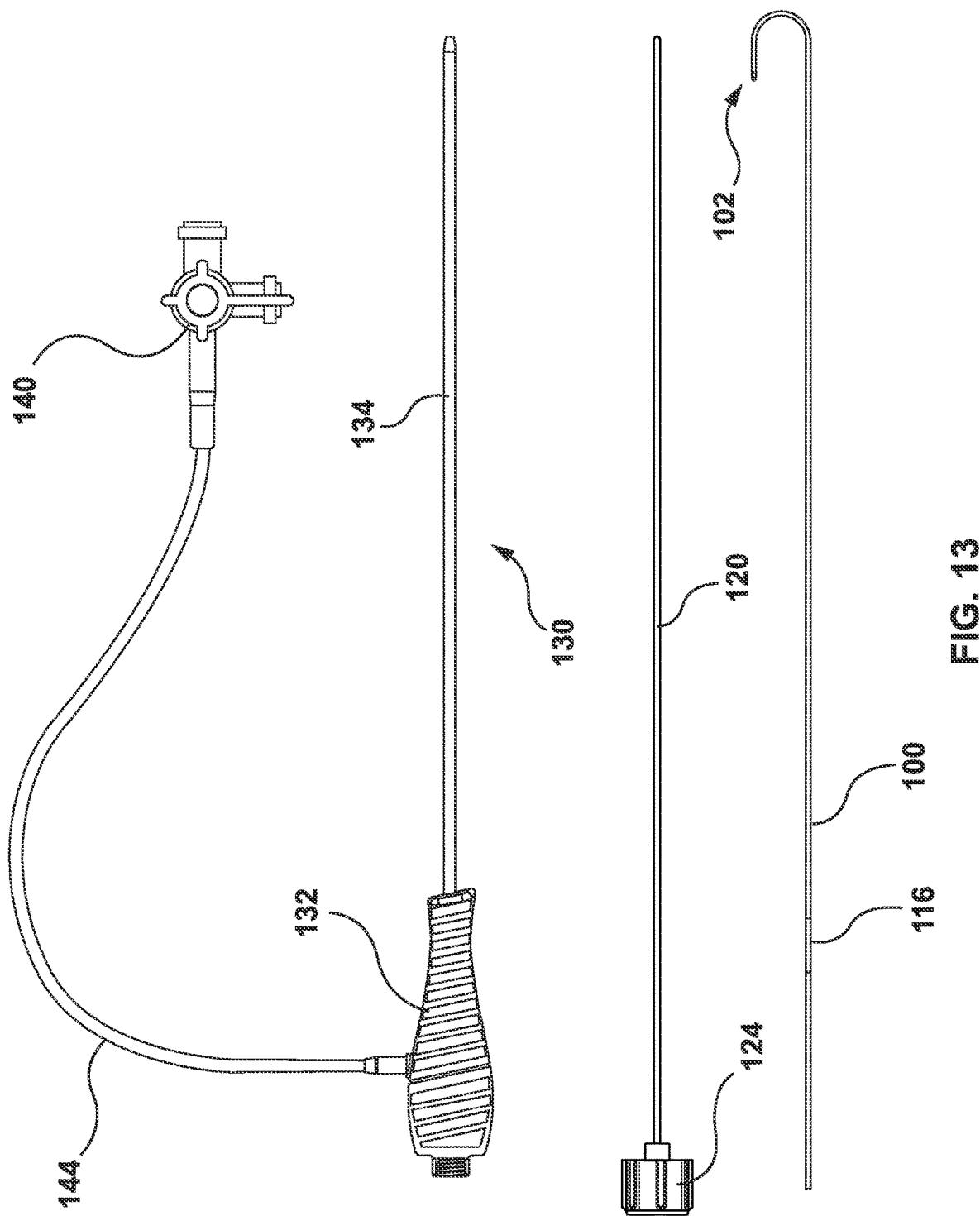
FIG. 13 is an illustration of apparatus in accordance with an embodiment of the present invention.

An example a system (or a kit) of apparatus suitable for performing the methods disclosed herein is shown in FIG. 13. The apparatus includes elongate puncture device 100, stylet 120, and introducer 130. While this disclosure uses the term "elongate puncture device" with regards to elongate puncture device 100 for explanatory purposes, elongate puncture device 100 is, in general, an elongate member capable of delivering energy to tissue through a distal end electrode. Elongate puncture device 100 is flexible in some embodiments and stiff in other embodiments. Examples of flexible embodiments include wires capable of delivering electrical energy, such as RF guidewires. Examples of stiff embodiments include needles operable for gaining access to pericardial cavities (some of which have a form and feel which resembles a 17Ga-20Ga Tuohy needle) or for gaining transseptal access (some of which have a form and feel which resembles a Brockenbrough needle). Also, typical embodiments of elongate puncture device 100 are operable to deliver electrical energy at frequencies other than radiofrequency. The energy frequency used in a given procedure is typically determined by the user selecting a frequency from the range of frequencies available with the generator being used in the procedure.

Introducer 130 of FIG. 13 is connected to valve 140 by tubing 144. In the illustrated embodiment, valve 140 is a 3-way stopcock valve. Alternative embodiments have other valve configurations that are operable to deliver and withdraw fluid. The apparatus of FIG. 13 may be used for a variety of tissue puncture procedures, for example, pericardial puncture procedures or transseptal puncture procedures. The main components of the apparatus shown in FIG. 13 are described in greater detail below.

Figures 1, 20:
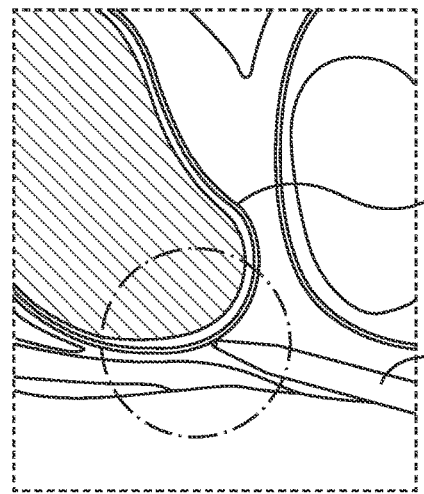

Referring to FIG. 1, an embodiment of elongate puncture device 100 comprises a distal end portion 110 which has a J-profile and a straight portion 112 at the distal end thereof. The elongate puncture device assumes the J-shape when not constrained. The J-profile of the distal end portion 110 helps minimize tissue trauma when tracking the distal tip across the heart's surface. The distal end portion 110 could also be a 'P' or a straight profile. Some embodiments have a distal tip angle from 0 to 35 degrees from the longitudinal axis of the main shaft. The idea is to keep the distal tip's straight portion 112 tucked in as it tracks around the heart to prevent it from swinging out and impinging adjacent soft tissue structures. The distal curve should also be in-plane with the wire body for predictable advancement of the device. One embodiment has a J-profile with an outside diameter of 10-12 mm. The straight portion 112 of the distal tip allows for alignment and orientation of the elongate puncture device tip to the introducer to facilitate RF puncture. One embodiment has a length of straight active tip which is between 6-9 mm in length. This length is required to allow the user to control alignment of the elongate puncture device by hand. Distal tip straight portion 112 has adequate body length to allow for alignment, positioning of the tip with respect to the introducer.

Electrode 102 is at the end of straight portion 112. The guidewire has a blunt electrode at the tip to safely dock with tissue and thereby facilitate directly delivering RF energy to the targeted tissue which the electrode is in contact with. Typically, the electrode 102 has a dome profile which minimizes the opportunity for premature mechanical puncture and allows the elongate puncture device to dock with the target tissue at various angles. Embodiments of electrode dome 103 may have a shape which is hemispherical, ellipsoid, or a paraboloid. In some embodiments, electrode dome 103 retains radiopaque marker 104. In alternative embodiments, other orientations and materials are used to secure radiopaque material to the distal end of elongate puncture device 100. Referring to FIG. 2, the proximal end portion of elongate puncture device 100 (I.e. the end which is at the end opposite to the end of the wire having electrode 102) is uninsulated and is operable for connecting to a power supply or generator. In some embodiments, the proximal end electrically exposed mandrel 108 is about 7.5+/−2.5 mm in length. In typical embodiments, the mandrel 108 is electrically conductive, and a proximal end portion of the mandrel 108 is uninsulated and operable for connecting to a power supply such that the distal tip electrode 102 is in electrical communication with the power supply, whereby energy can be delivered through the distal tip electrode 102 to tissue and the distal tip electrode enables recording epicardial EGM.

Elongate puncture device 100 of FIG. 13 includes a proximal marker 116. Laser etching can be used to form proximal marker 116 so that it cannot be removed during use or sterilization. The use of proximal marker 116 is described below.

Some embodiments of elongate puncture device 100 comprises a mandrel 108 which is electrically conductive and covered by a clear layer of insulation 114 (clear heat-shrink 115), the clear layer stopping short of a distal end of the mandrel 108 such that such that the distal end of the mandrel 108 is electrically exposed (i.e. not covered) to define a distal tip electrode 102. A portion of mandrel 108 is surrounded by a visible marker 117, with the visible marker being covered by the clear layer, wherein the portions of the elongate puncture device at and adjacent the visible marker 117 have a constant outer diameter.

Some embodiments of elongate puncture device 100 include one or more marker 117 formed by mechanical grinding of an oxide coating of the wire created during heat treatment of the wire to fine-tune transformation temperatures. Marker 117 can be a proximal marker, an intermediate marker, or a distal marker. The formation of said markers is described referring to FIGS. 22A and 22B. FIG. 22b shows a cross-section of wire at point "A" of FIG. 22A after the wire is heat treated. FIG. 22B illustrates elongate puncture device 100 comprising a solid mandrel 108 surrounded by oxide coating 118 which is covered by clear heat-shrink 115 (a clear layer). In typical embodiments mandrel 108 is comprised of nitinol while in some alternative embodiments it is stainless steel. The typical oxide coating 118 on the wire is a titanium dioxide (TiO(2)) oxide layer. This coating is typically stable and acts as a barrier against ion exchange. After the heat treatment, oxide coating 118 extends the full length of the wire. Typically, a portion of the coating at the proximal end is removed to allow electrical connection with the over wire cable connectors and at least one other portion of the coating is removed to form a marker visible without imaging i.e. visible to an unaided eye. The oxide coating 118 can be removed by grinding the surface of the wire to the desired profile to thereby form a marker 117. Clear heat-shrink 115 typically comprises a Clear PTFE formed from an extruded tube that that is heat shrunk onto the wire. The configuration of the markers of elongate puncture device 100 maintain a smaller consistent outer diameter (i.e. do not increase the outer diameter) while maintaining electrical integrity by including the markers under clear heat-shrink 115. Alternative embodiments of heat-shrink 115 are comprised of a clear layer formed from alternative materials known to those skilled in the art. The elongate puncture device 100 is electrically insulated by the clear heat-shrink which allows a marker 117 to be visible. In some examples, the clear layer has a thickness ranging from about 0.086 mm to 0.118 mm.

Figure 22A:
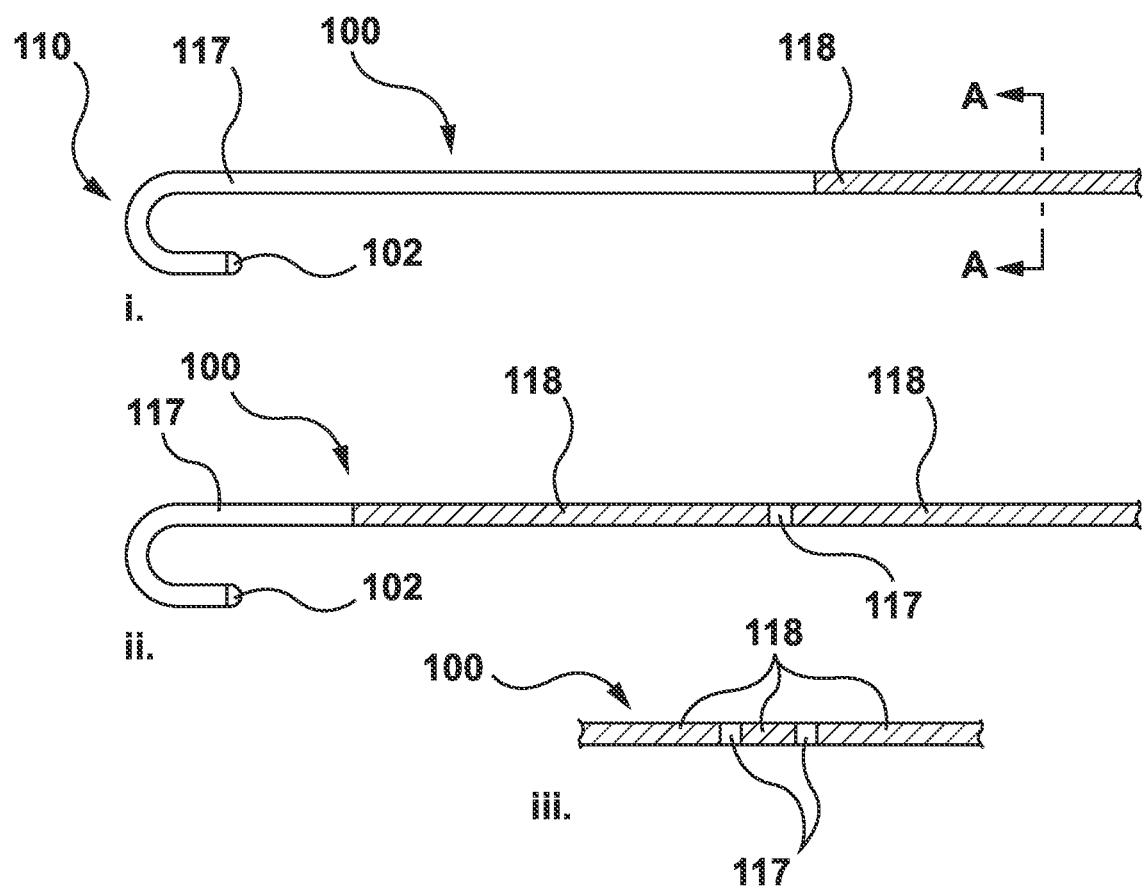
FIG. 22A is an illustration of different maker configurations of an elongate puncture device.
Figure 22B:
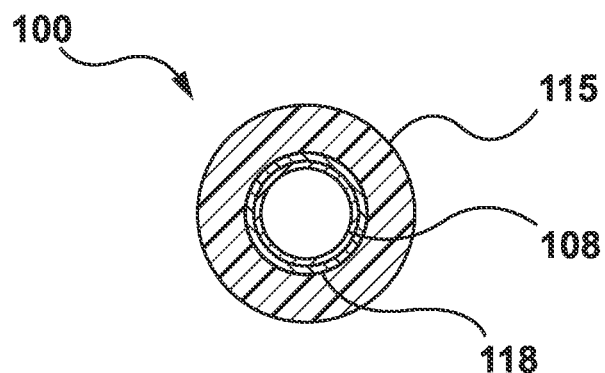
FIG. 22B is a cross section of FIG. 22A at point "A"

FIG. 22A shows different examples of marker 17. FIG. 22A-i shows a distal end marker 117. FIG. 22A-ii shows a distal end marker 117 and an intermediate marker 117. FIG. 22A-iii shows two intermediate markers 117. Proximal marker 116 of FIG. 17 could be formed by removing an oxide as described above and covering the wire with a clear layer. In some such embodiments, visible marker 117 comprises at least one portion of the mandrel wherein the oxide coating is applied directly to the mandrel i.e. in direct contact with the mandrel.

Figure 3:
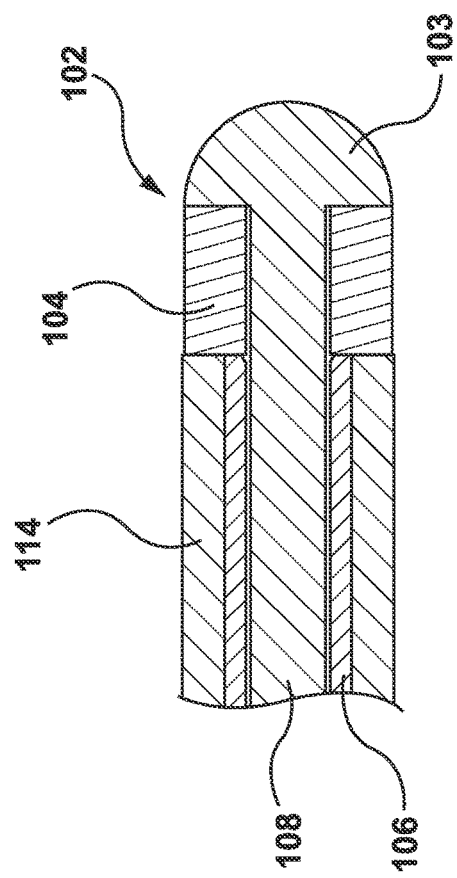
FIG. 3 is an illustration of a detail of FIG. 2.

FIG. 3 illustrates detail C of FIG. 2. The embodiment of FIG. 3 includes a mandrel 108 (outer diameter 0.011 inches or 0.28 mm) with a radiopaque coil 106 (outer diameter 0.017 inches or 0.43 mm) covering a portion thereof. Insulation 114 (outer diameter 0.028 inches or 0.71 mm) covers the mandrel 108 and the radiopaque coil proximal of electrode 102 to enable delivery of electrical energy through electrode 102 (outer diameter 0.0275 inches or 0.70 mm, radius 0.01375 inches or 0.35 mm). In some embodiments the electrical insulation is comprised of heat-shrink (e.g. polytetrafluoroethylene (PTFE)). Radiopaque coil 106 extends around the curve of distal end portion 110 (FIG. 2). A radiopaque coil aids the physician in determining location of the distal tip of the elongate puncture device while using fluoroscopy. Physicians may reduce fluoroscopy intensity for long procedures reducing visibility of the guidewire. The coil can also improve echogenic properties when using ultrasound to visualize the guidewire tip. The coil can be 3 cm or longer. The coil also aids in visualizing the guidewire track around the cardiac silhouette. The coil aids to better visualize the distal tip's 1' profile and how it interacts within the space. It can aid physicians in helping determine evidence of adhesions or anatomical abnormalities. The RO coil may be longer or shorter than 3 cm and may be constructed of various materials such as platinum, titanium, gold and tungsten. Some embodiments comprise a radiopaque coating around the mandrel. In some such embodiments, the wire is coated with a thin precious metal. Distal to radiopaque coil 106, electrode 102 includes a radiopaque marker 104 (outer diameter 0.0275 inches or 0.70 mm, inner diameter 0.011 inches or 0.28 mm, length 0.020 inches or 0.51 mm) which surrounds mandrel 108. Radiopaque marker 104 can also be referred to as a radiopaque (RO) band or a puck. A Radiopaque marker 104 helps visualize location of the tip under fluoroscopy. The RO band can help confirm if the tip of the elongate puncture device is protruding from the tip of the introducer 130. Embodiments of the RO band may be of varying lengths and constructed of various materials such as platinum, titanium, gold and tungsten. Elongate puncture device 100 is also visible using ultrasound imaging systems, radiopaque coil 106 being particularly echogenic.

Electrode 102 also includes an electrode dome 103 which may be formed by laser welding. In typical embodiments the mandrel of the wire, mandrel 108 is comprised of a shape memory material (e.g. nitinol) whereby mandrel 108 is kink resistant. The guidewire, when introduced into the pericardial space, may undergo sharp deflections. The flexible mandrel prevents any kinking, mitigating the possibility of getting the guidewire trapped in the body. In some alternative embodiments, mandrel 108 is constructed of stainless steel, which is less kink resistant. In other alternative embodiments, the mandrel is made of other super elastic materials with varying dimensions and cross-sections. In some embodiments, radiopaque coil 106 is comprised of tungsten. Some typical embodiments include radiopaque marker 104 being comprised of a mixture of platinum and iridium (e.g. 10% iridium), and electrode dome 103 being comprised of nitinol which has been dome welded. The distal tip region is floppy (i.e. not rigid) to minimize tissue trauma when tracking across the hearts surface. To achieve this, the mandrel at the distal end portion reduces in diameter necks from 0.025" (0.64 mm) down to 0.006" (0.15 mm) over a length of 25 cm. The tip will deflect creating a secondary bumper to that of the 'J' tip profile.

Elongate puncture device 100 has a length of about 150 to about 180 cm to ensure the guidewire can be deployed into the pericardial space and wrap around 1 to 2 times around the heart to define the cardiac silhouette under fluoroscopy. Alternative embodiments of the wire have a smaller or larger length to accommodate varying patient sizes and BMIs e.g. lengths of 120 to about 180 cm. The elongate puncture device 100 typically has lubricous coating to ensure the guidewire tracks smoothly around the heart within the pericardial space.

Figure 25:
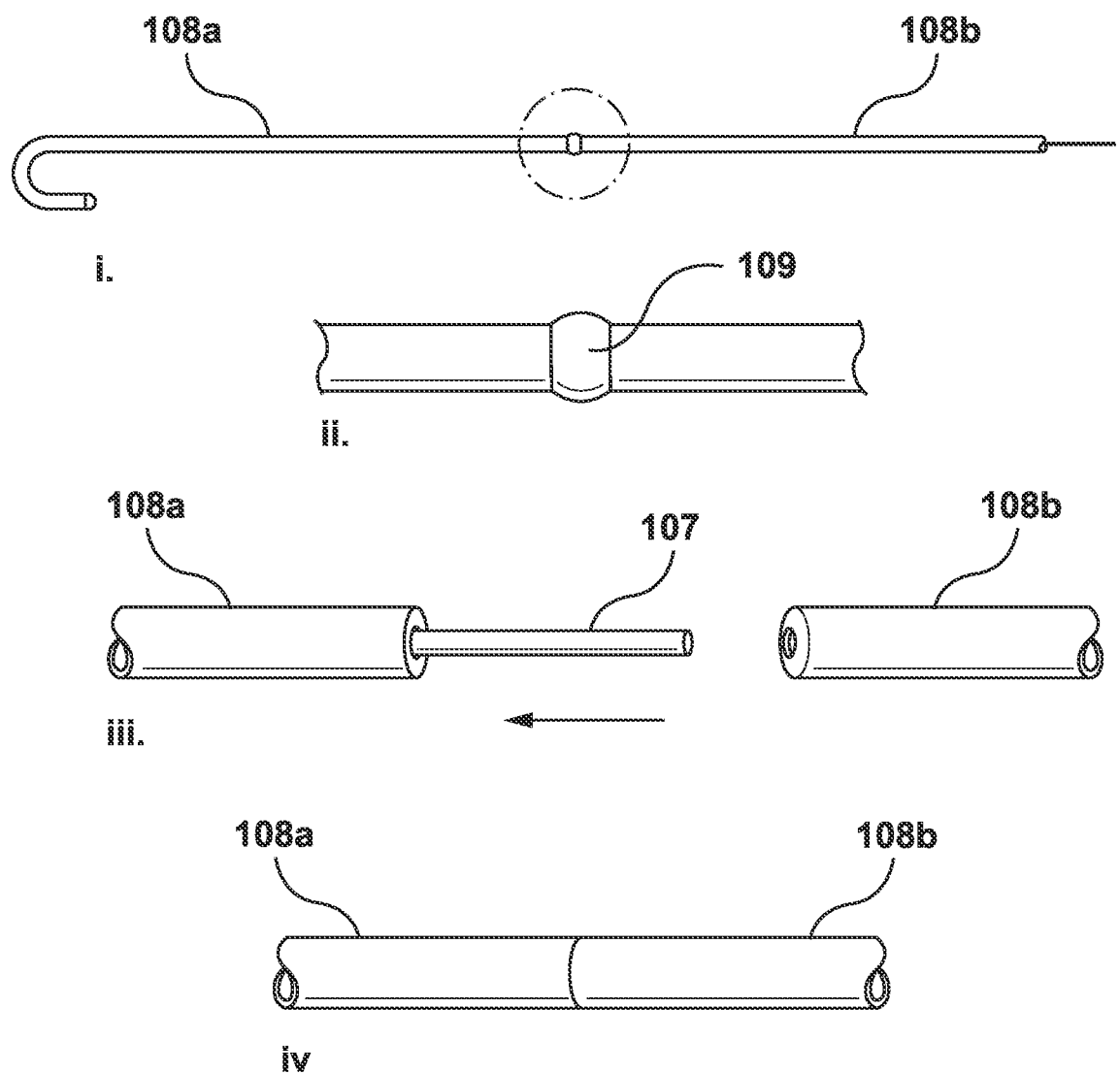
FIG. 25 is an illustration of an alternative embodiment of a mandrel.

In some embodiments, the shaft of elongate puncture device 100, radiopaque marker 104, and proximal marker 116 have outer diameters <=0.035" (0.89 mm). Radiopaque marker 104 is comprised of platinum and iridium (Pt/Ir) and has an inner diameter >=0.01" (0.25 mm). Mandrel 108 of the guidewire is made of Nitinol designed to be kink resistant. An alternative embodiment (FIG. 25) is a composite of super elastic material such as Nitinol to provide a flexible kink resistant distal tip portion 108a and a proximal wire portion 108b of a stiffer alloy such as stainless steel. These materials can be welded (e.g. weld 109), press fit or glued together using an inner mandrel section 107 which extends from distal tip portion 108a in the example of FIG. 25. In further alternative embodiments, inner mandrel section 107 extends from proximal wire portion 108b.

The body of the guidewire (elongate puncture device 100) is insulated with polytetrafluoroethylene (PTFE). While typical embodiments of elongate puncture device 100 have an outer diameter of <=0.035" (0.89 mm), any size outer diameter of the guidewire is acceptable as long as it fits within the dilator used for an epicardial procedure. Alternative embodiments of radiopaque marker 104, which are components of smaller diameter elongate puncture devices, have an inner diameter smaller than 0.01" (0.25 mm). While a typical embodiment of introducer 130 has an inner diameter of >=0.035" (0.89 mm), other inner diameter sizes of the introducer are possible so long as the elongate puncture device 100 used in a procedure can pass through.

FIG. 4 is an illustration of an embodiment of stylet 120 which includes stylet mandrel 122 and stylet cap 124. In alternative embodiments, the tip is sharp. Some alternative embodiments do not include adhesive 126.

Figure 24:
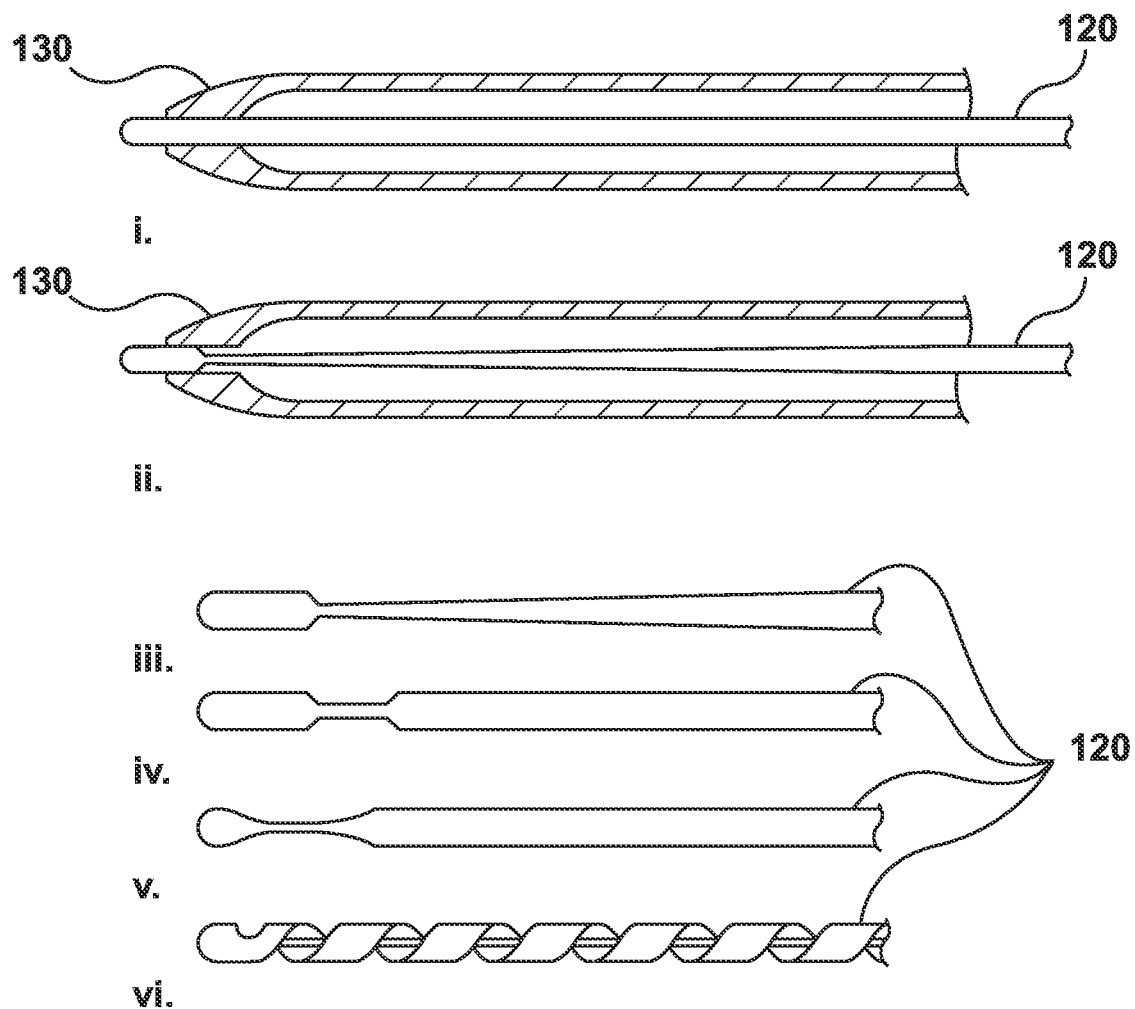
FIG. 24 is an illustration of a different stylet embodiment.

FIG. 5 is a cross sectional view of the embodiment of FIG. 4 which includes internal details of stylet cap 124, and adhesive 126. FIG. 6 is an illustration of detail A of FIG. 4 showing rounded end 128. In alternative embodiments (FIG. 24, ii to v) the cross section varies along the length of the stylet 120 necking down (or tapering) towards the distal tip to allow better flow of contrast or fluids through the tip of the introducer when the stylet is installed. FIG. 24$i$ illustrates a non-tapered stylet 120 inside of an introducer 130. FIG. 24$vi$ illustrates a spiral embodiment of stylet 120.

Figure 7:
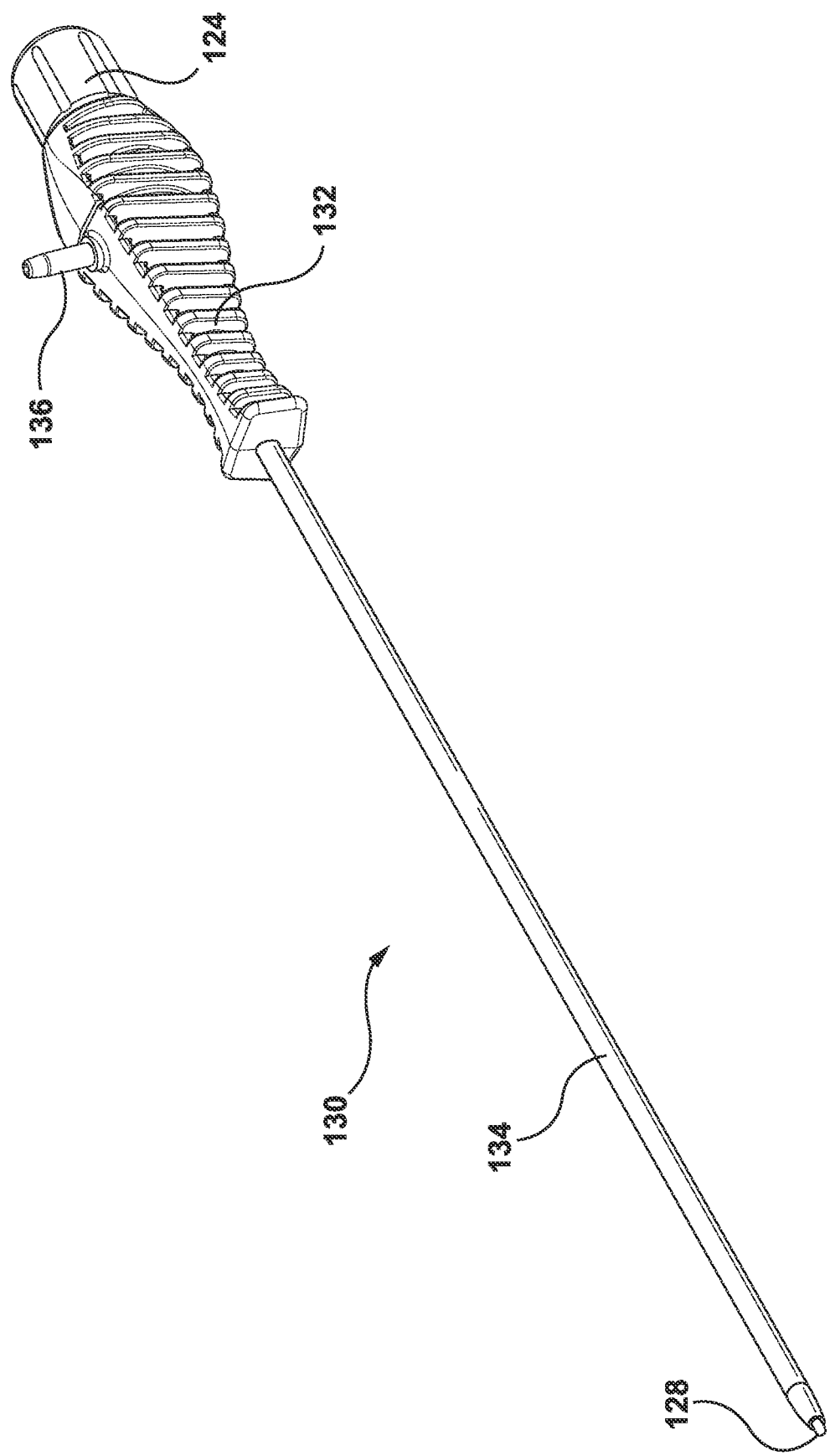
FIG. 7 is a perspective view of an introducer with a stylet contained therein in accordance with an embodiment of the present invention.

FIG. 7 shows an embodiment of an introducer 130 with a stylet contained therein. Introducer 130 includes an introducer shaft 134 connected to hub 132. Hub 132 has a male side port 136 for connecting to tubing 144 (FIG. 13) and a receiving opening (FIG. 16) for receiving a stylet or wire. Alternative embodiments have other side port configurations that are operable to deliver and withdraw fluid. Stylet cap 124 of the installed stylet is proximal of hub 132 and rounded end 128 of the stylet is distal of introducer shaft 134. In some embodiments introducer shaft is a reinforced 8Fr shaft covered with high-density polyethylene (HDPE) comprised of 20% $BaSO_4$ (Barium Sulfate) which is radiopaque. The introducer 130 is operable to accommodate the flexible elongate puncture device allowing the introducer 130 (with a elongate puncture device inserted therein): traverse through adipose tissue to reach the target tissue; facilitate the delivery of RF energy by supporting the proper alignment, orientation and position of the distal tip of a elongate puncture device; and allow the guidewire to be deployed into the pericardial space.

Figure 28:
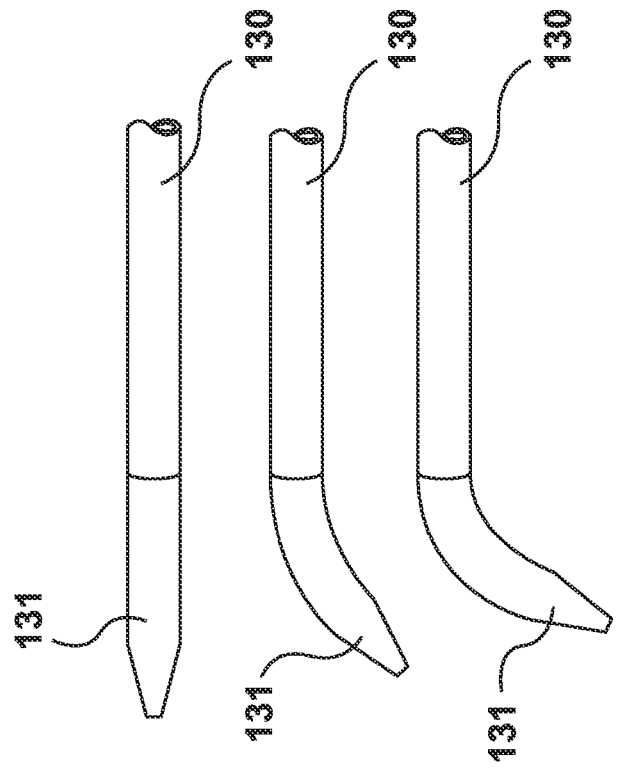
FIG. 28 is an illustration of alternative embodiments of the introducer distal tip.

Alternative embodiments of the introducer distal tip 131 may be straight, curved or bent between 15-45 degrees, such as in the examples of FIG. 28. A curved or bent tip would allow the ability to align, orientate and position the distal tip of the elongate puncture device more tangential to the cardiac silhouette.

Figure 26:
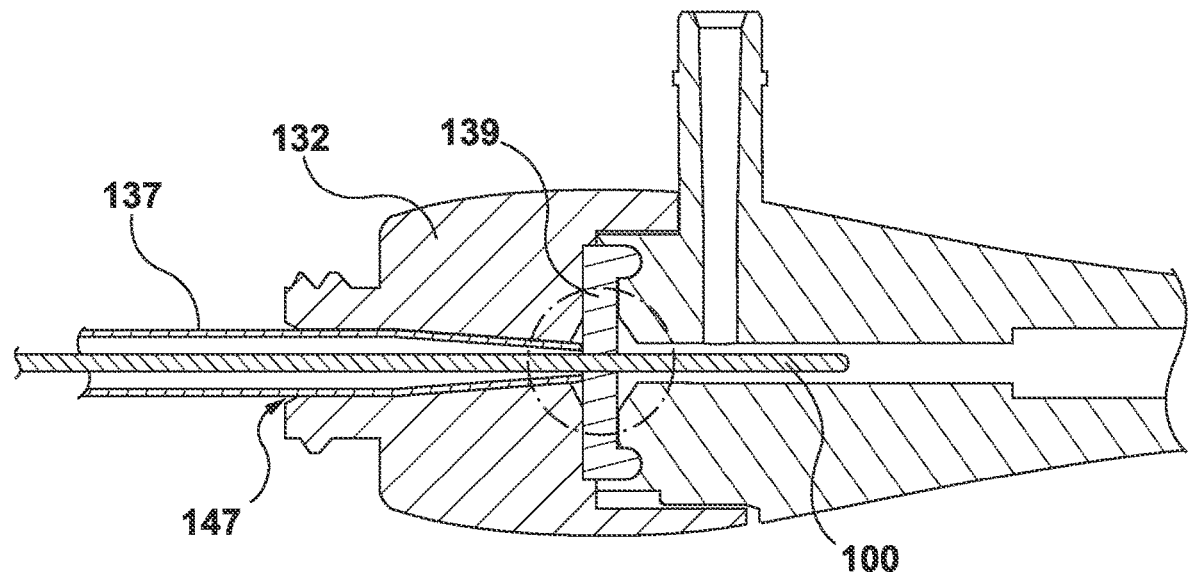
FIG. 26 is an illustration of an introducer hub with a tip straightener.
Figure 27:
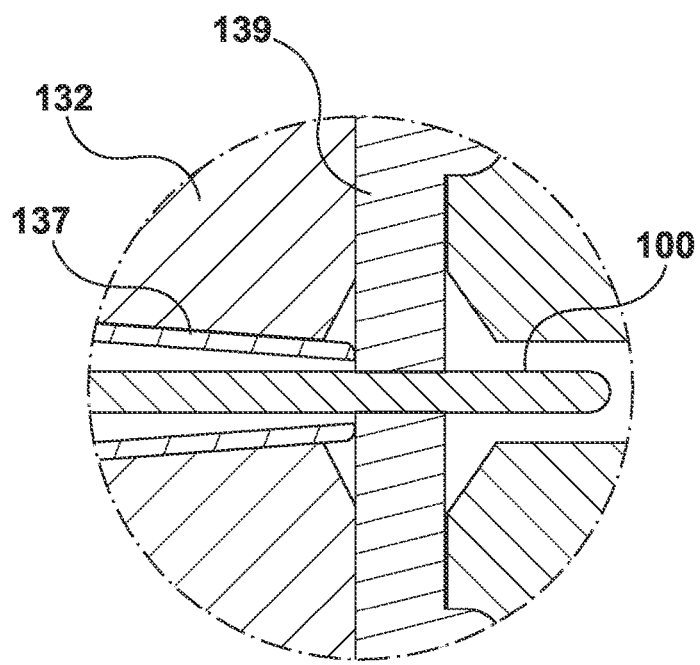
FIG. 27 is an enlarged view of a portion of FIG. 26.

The introducer is designed to allow 'front loading', the insertion of the guidewire through the proximal hub and/or 'back loading', through the distal tip of the introducer. Alternative embodiments allow only certain compatible guidewires to limit use. Referring to FIG. 26 and FIG. 27, a tip straightener 137 with a distal tip radius of less than 0.057" (1.45 mm) allows for insertion of elongate puncture device 100 through receiving opening 147 and valve 139 and into the introducer proximal hub 132 inside diameter. This allows the distal tip of the introducer to gain close approximation to the valve to facilitate seamless guidewire insertion.

Alternative embodiments of the introducer can accommodate and introduce multiple guidewires for ease of downstream work flow. Such introducers can accommodate multiple guidewires up to 0.014 inches or 0.018" in diameter, for example, if the inner diameter of the introducer is 0.035 inches (0.89 mm).

Figure 23A:
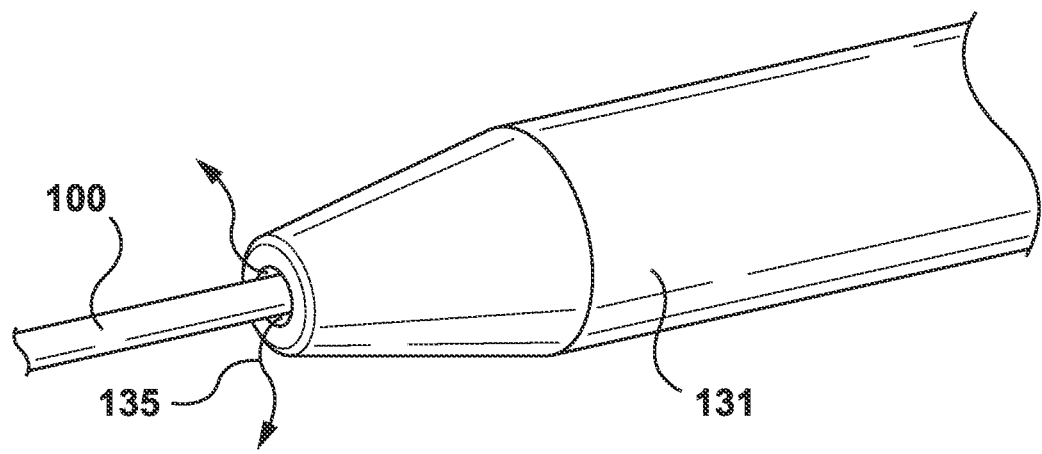
FIG. 23A is an illustration of fluid flow from a radial gap at a distal end if an introducer.
Figure 23B:
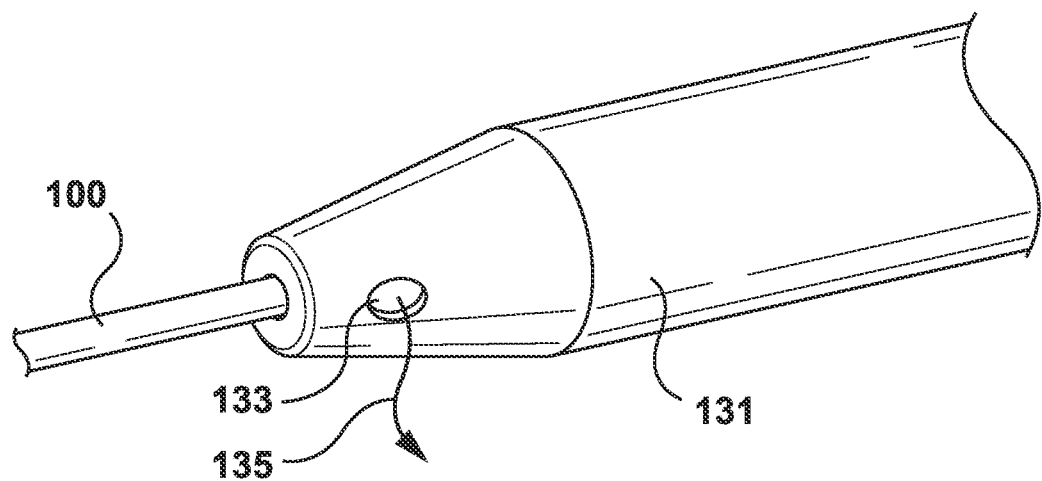
FIG. 23B is an illustration of an introducer with a side port for fluid flow.

The introducer 130 and elongate puncture device 100 are configured such that introducer 130, even with an inserted elongate puncture device, can deliver and withdraw fluid while cannulating the elongate puncture device. Introducer shaft 134 is typically >=5 inches (12.7 cm). In one embodiment (FIG. 23A), the radial gap between introducer tip 131 ID and the elongate puncture device 100 OD is >0.001 inches (0.025 mm) to provide adequate contrast flow 135 (>15 ml/min at 10 PSI (or 69 Kilo Pascal)) wherein contrast flow 135 is measured by delivering fluid by hand into a beaker for a minute at a constant 10 psi (69 Kilo Pascal) and then measuring the volume of fluid at the end of that minute. In one such embodiment, the introducer tip lumen ID is 0.0385 (0.978 mm)+/−0.0005 inches (0.013 mm), and the maximum elongate puncture device OD is 0.0350 (0.889 mm)+/−0.0005 inches (0.013 mm), whereby the minimum gap with this geometry is 0.00125" (0.032) mm. Another embodiment (FIG. 23B) of the introducer has side port 133 located at the introducer tip 131 to allow contrast flow 135. The introducer shaft 134 has a length that is operable to provide adequate stiffness and control to the physician, and to reach the pericardial sac while providing a handle outside of the patient's chest wall. In alternative embodiments, Introducer shaft 134 is less than 5" (12.7 cm). To provide adequate reach and controlled linear trajectory, one embodiment of introducer 130 has a shaft of about 15 cm and a stiffness >0.04 Nm2 and for a shaft 12 cm a stiffness >0.03 Nm2. Another alternative length is from 4 to 6 cm to accommodate younger children and is from 7 to 10 cm for older children.

Figure 29A:
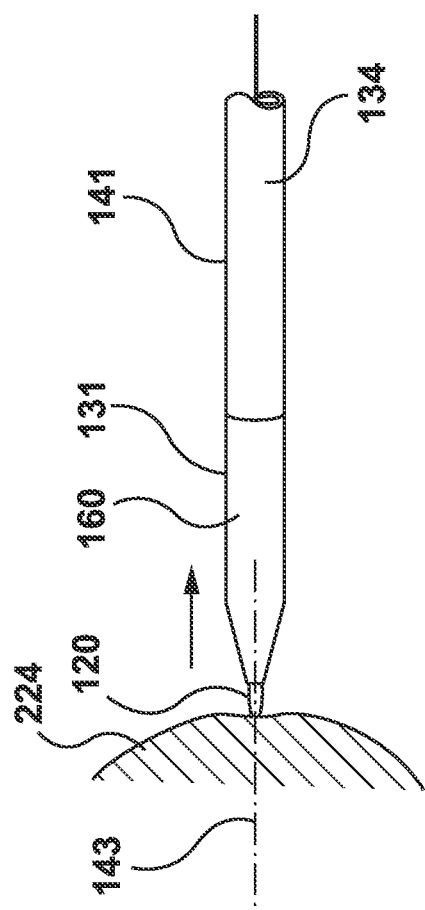
FIG. 29A is an illustration of an introducer with a flexible tip and an inserted stylet.
Figure 29B:
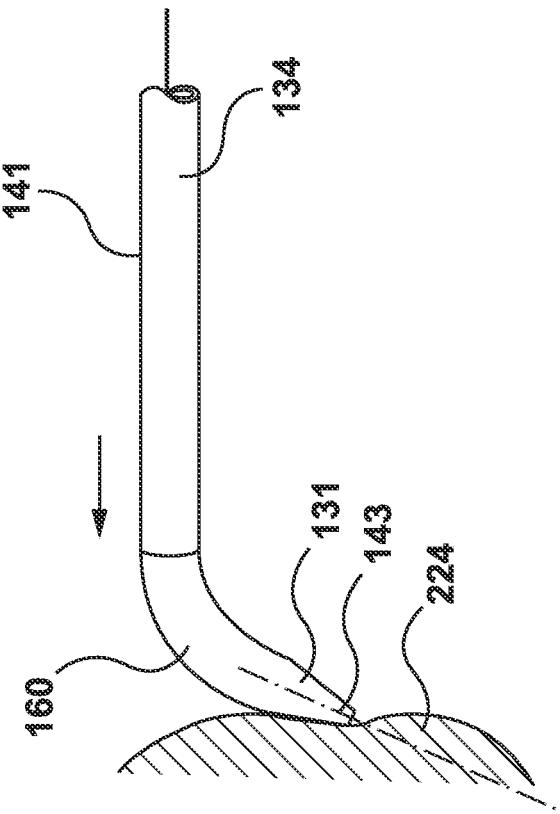
FIG. 29B is an illustration of the introducer of FIG. 29A with the stylet removed.

Alternative embodiments (FIG. 29A and FIG. 29B) of the introducer 130 include the introducer shaft 134 having a rigid portion 141 and the distal tip 131 beings flexible, forming a flexible tip portion 160. In some embodiments flexible tip portion 160 is 2-3 cm in length. In FIG. 29A the tip is supported by the rigid distal tip of the stylet 120 to facilitate the introducer traversing through adipose tissue. In FIG. 29A the central axis 143 of the tip is perpendicular to the surface of heart 224. However, once the stylet is removed (FIG. 29B), the distal tip of the introducer is unsupported, and flexible. In FIG. 29B the central axis 143 of the tip is closer to being parallel to the surface of heart 224 than in FIG. 29A. A flexible tip allows alignment, orientation and positioning of the elongate puncture device to be more tangential to the cardiac silhouette (FIG. 29B), instead of a perpendicular approach (FIG. 29A). Some embodiments of introducer 130 include pull wires which are operable to create a bend in flexible tip portion 160.

Figure 34A:
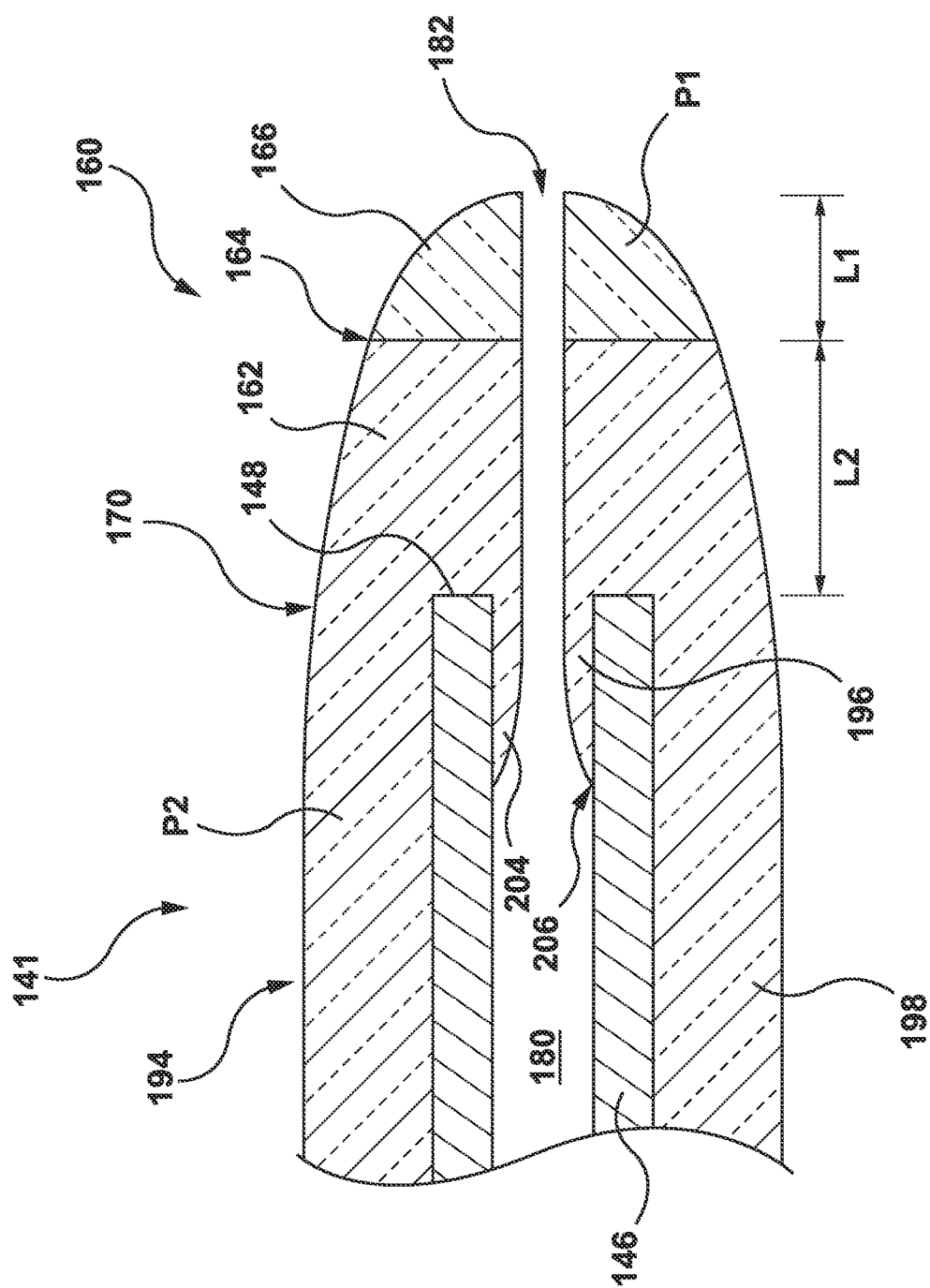
FIGS. 34A and 34B are cross-sectional views of another embodiment of the introducer of FIG. 31.
Figure 35:
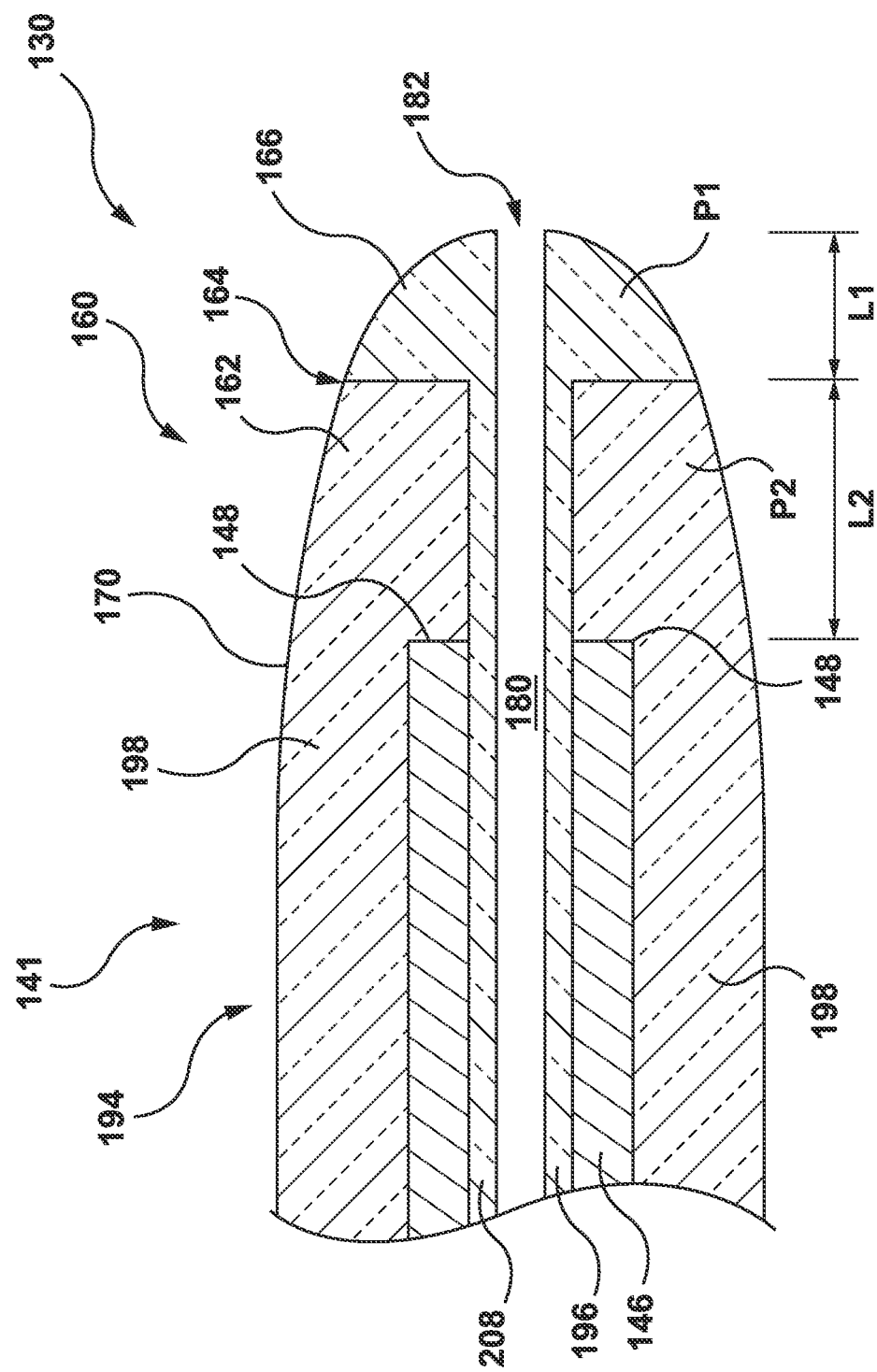
FIG. 35 is cross-sectional view of another embodiment of the introducer of FIG. 31.
Figure 36:
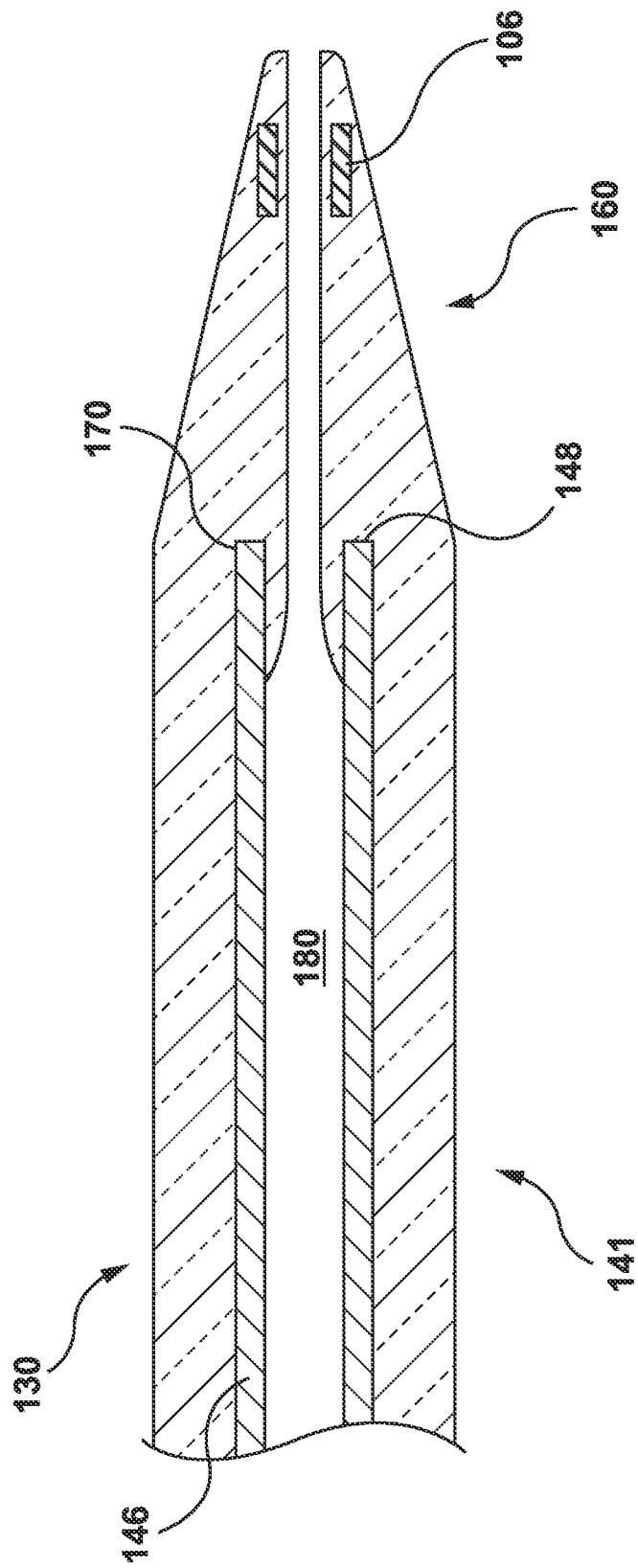
FIG. 36 is a cross-sectional view of an embodiment of the introducer of FIG. 29 having a tip marker.

FIG. 36 is a cross-sectional view of an embodiment of the introducer 130 of FIG. 29 having a tip marker comprising a radiopaque coil 106. Flexible tip portion 160 is distal of rigid portion distal end 170 which is defined by metal tube distal end 148. The embodiment of FIG. 36 has only one type of polymer. Alternative embodiments include a first polymer P1 and a second polymer P2 arranged in the configurations illustrated in FIGS. 31 to 35 wherein the tip marker is completely contained in flexible tip portion cap 166 or only partly contained in flexible tip portion cap 166.

Figure 37:
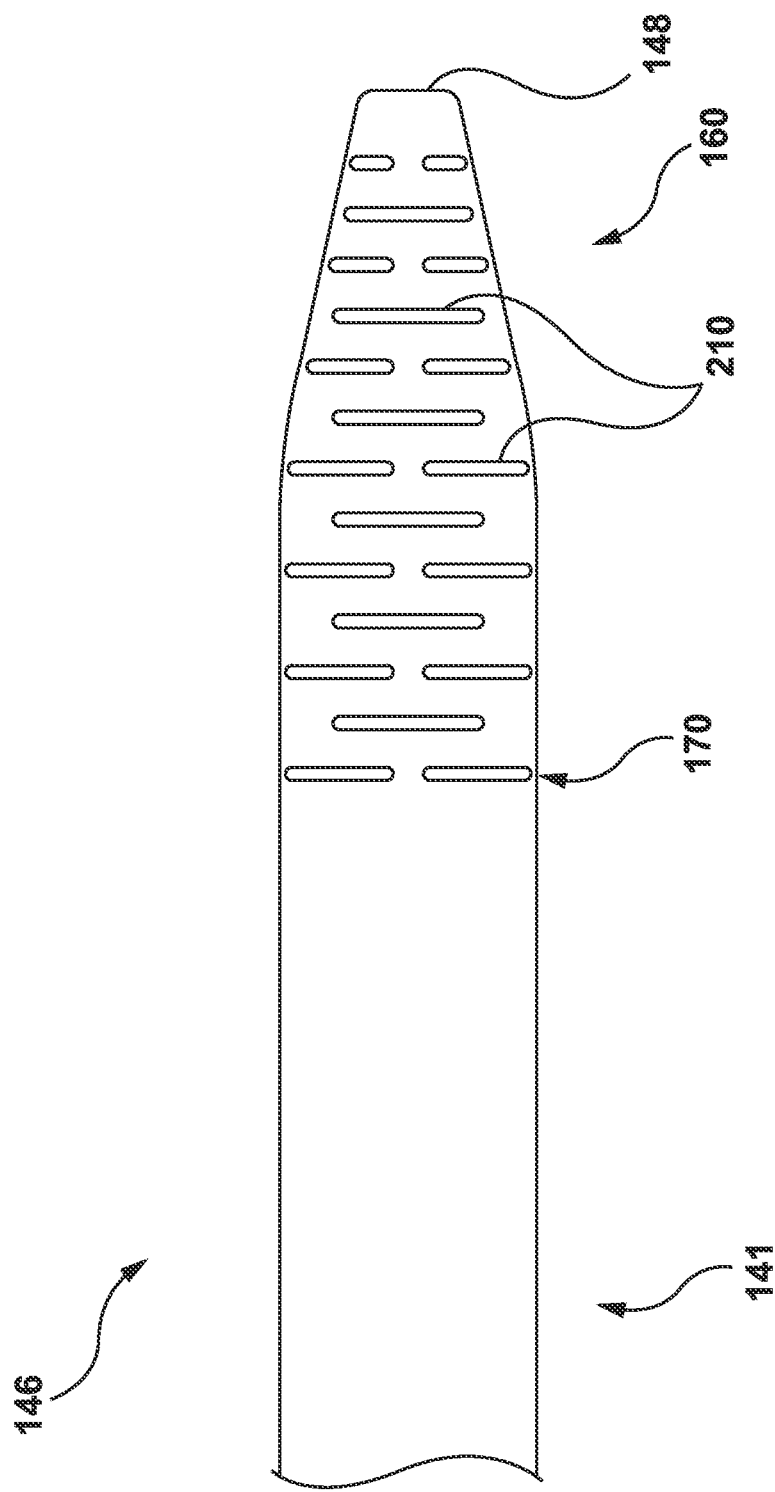
FIG. 37 is a side view of an internal metal tube of another embodiment of the introducer of FIG. 29 having laser cuts therein.

FIG. 37 is a side view of an internal metal tube 146 of another embodiment of the introducer of FIG. 29. Metal tube 146 has laser cut slots 210 therein. The rigid portion 141 has rigid portion distal end 170 at the most proximal of the slots 210. The metal tube 146 of flexible tip portion 160 includes a plurality of slots 210 cut therein which provide for flexibility of the tube. In alternative embodiments, slots 210 are cut by means other than laser.

Figure 38:
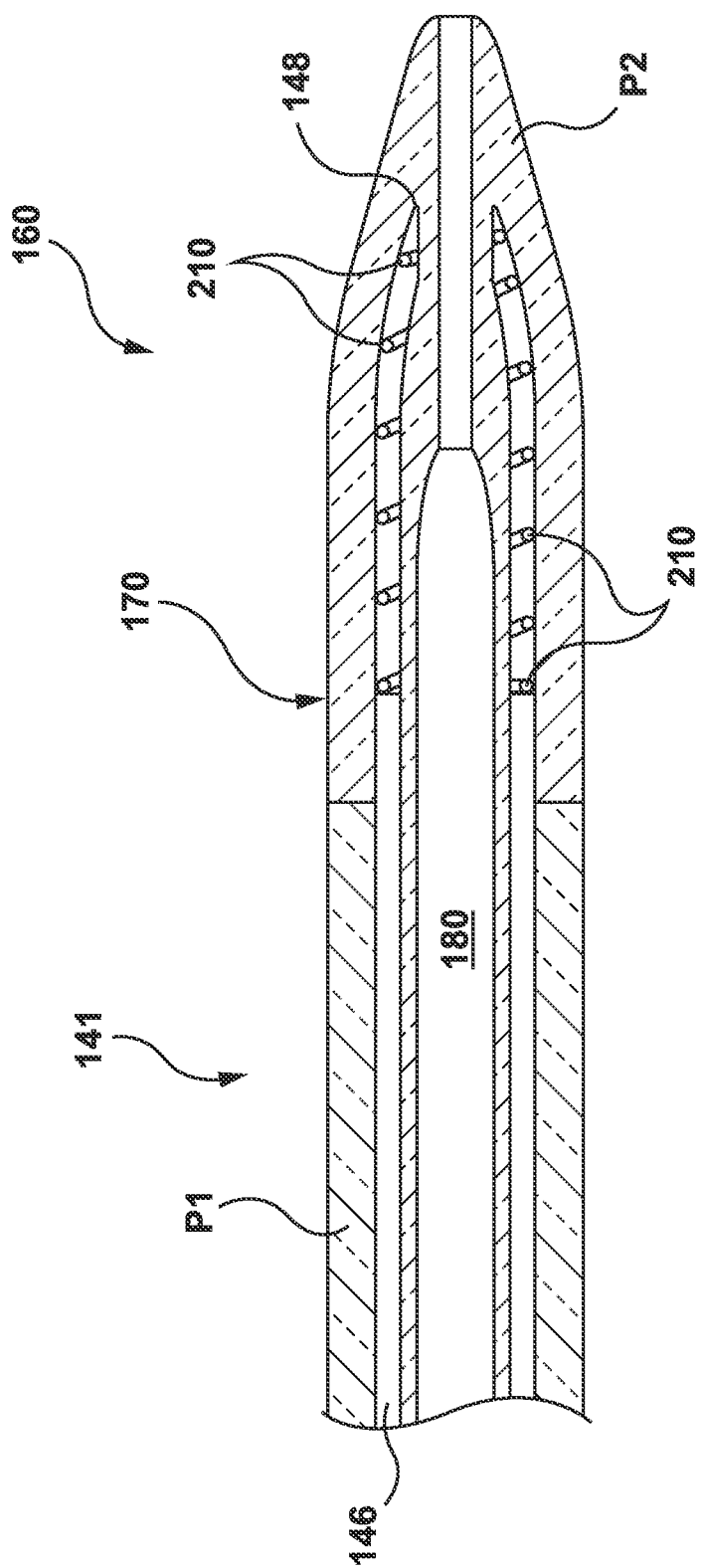
FIG. 38 is a cross-sectional view of an embodiment of an introducer having the metal tube of FIG. 37.

FIG. 38 is a cross-sectional view of an embodiment of an introducer having the metal tube 146 of FIG. 37 with laser cuts slots 210 therein. The most proximal laser cut slot 210 is at rigid portion distal end 170 which defines the boundary between rigid portion 141 and flexible tip portion 160. Metal tube 146 ends distally at metal tube distal end 148. The example of FIG. 38 includes first polymer P1 and second polymer P2.

FIG. 31

Figure 31:
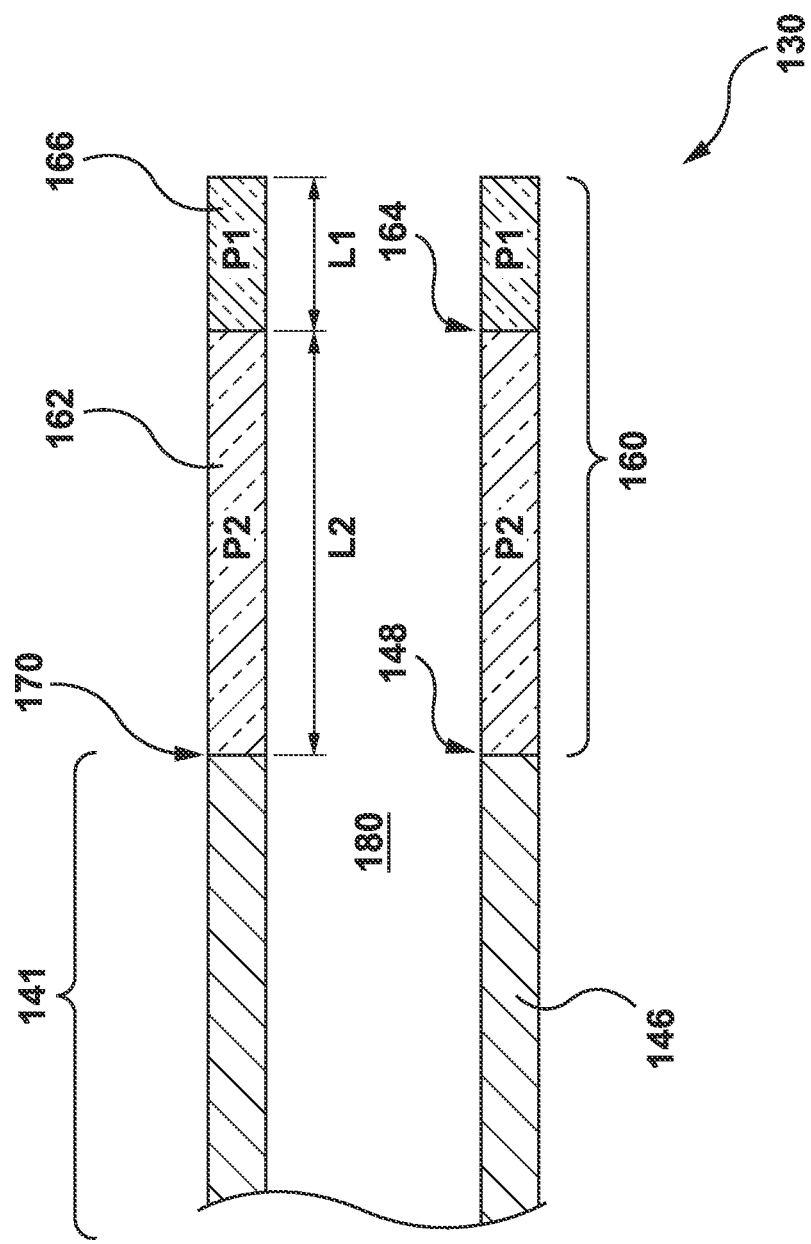
FIG. 31 is a cross-sectional diagrammatic view of an embodiment of introducer in accordance with an embodiment of the present invention.

FIG. 31 is a diagrammatic view of an embodiment of introducer 130 having features which allow it to be used in the manner illustrated in FIGS. 29A and 29B. FIG. 31 illustrates a surgical introducer 130 comprising an introducer shaft having a rigid portion 141 and a flexible tip portion 160. The rigid portion 141 has a rigid portion distal end 170 with a metal tube 146 extending to the rigid portion distal end 170 wherein the metal tube 146 has a metal tube distal end 148.

Referring to FIG. 31, the flexible tip portion 160 is distal of the metal tube distal end 148, with the flexible tip portion 160 including a first polymer P1 and a second polymer P2, wherein the second polymer P2 is more flexible than the first polymer P1. The second polymer P2 extends distally from the metal tube distal end 148 to define a second polymer flexible tip segment 162 having a second polymer flexible tip segment end 164. The first polymer P1 extends distally from the second polymer flexible tip segment end 164 to define a flexible tip portion cap 166. The rigid portion 141 and the flexible tip portion 160 define a lumen 180, and the flexible tip portion cap 166 defines a distal end opening 182 (FIG. 32A) which is in fluid communication with the lumen 180.

In the embodiment of the introducer 130 shown in FIG. 31, the second polymer flexible tip segment 162 has a length of length L2 and the flexible tip portion cap 166 has a length of length L1, wherein length L2 is greater than length L1.

FIGS. 32 to 35

FIGS. 32 to 35 illustrate different embodiments of the surgical introducer 130 of FIG. 31. It is typical in these embodiments for the distal end opening 182 to be forward facing and for an outside layer 194 of a polymer to be on the outside of the metal tube 146. In some embodiments the flexible tip portion 160 has a length of about 1 to 3 cm, while in other embodiments the flexible tip portion 160 has a length of about 2 to 3 cm. In typical embodiments, the first polymer P1 is HDPE and the second polymer P2 is LDPE. Other polymers are known to those skilled in the art can be used which can be selected to provide for the second polymer P2 being more flexible than the first polymer P1.

Referring to FIGS. 32 to 35, in some embodiments of surgical introducer 130, the metal tube 146 is comprised of steel, and in some examples is comprised of stainless steel. Typical embodiments further comprise the second polymer P2 extending proximally from the metal tube distal end 148 on an outside of the metal tube 146.

Figure 32A:
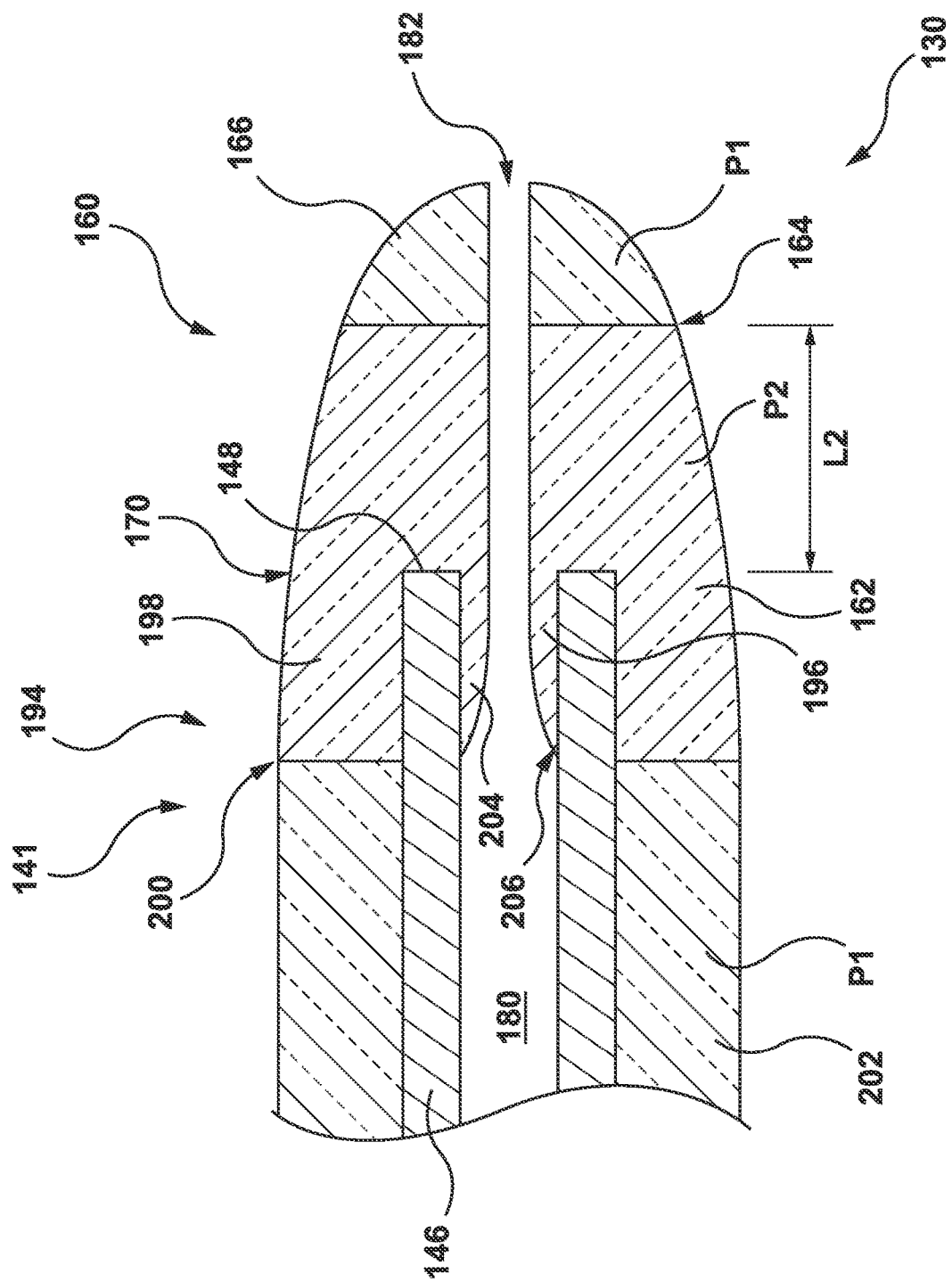
FIGS. 32A and 32B are cross-sectional views of an embodiment of the introducer of FIG. 31.
Figure 32B:
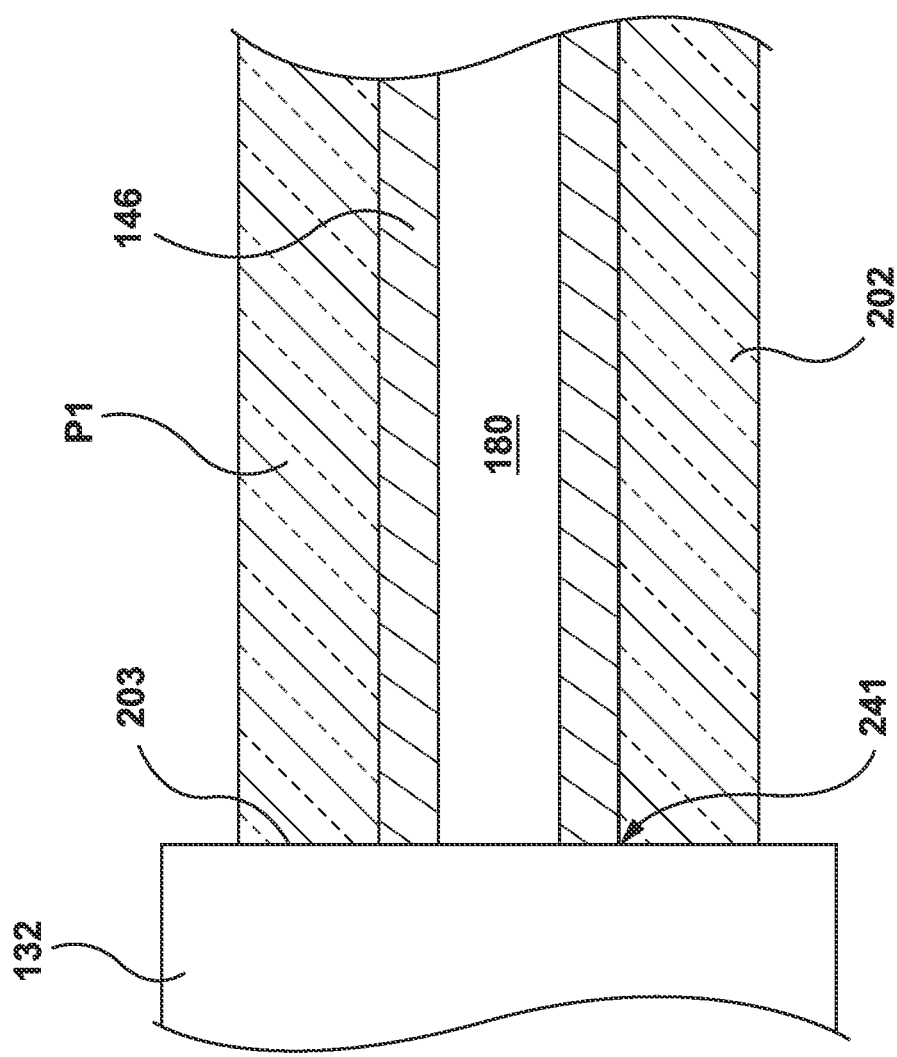

FIGS. 32A and 32B

Referring to the embodiment of FIG. 32A, the surgical introducer 130 comprises inside layer 196 of polymer on the inside of the metal tube 146 the distal portion of the metal tube. The second polymer P2 extends proximally from the metal tube distal end 148 on the outside of the metal tube 146 to define a second polymer outside layer 198 which has a second polymer outside layer proximal end 200, and the first polymer P1 extends proximally from the second polymer outside layer proximal end 200 on the outside of the metal tube 146 to define a first polymer outside layer 202. The second polymer flexible tip segment 162 has a length of length L2 (FIG. 31) and the second polymer P2 extends proximally from the metal tube distal end 148 on the outside of the metal tube 146 to define a second polymer outside layer 198 which extends longitudinally and proximally from the metal tube distal end 148 for a distance less than length L2. The second polymer P2 extending proximally from the metal tube distal end 148 on the inside of the metal tube 146 to define a second polymer inside layer 204 having a second polymer inside layer proximal end 206.

In some embodiments, the second polymer P2 is comprised of LDPE (low-density polyethylene) and the first polymer P1 is comprised of HDPE. LDPE is softer and more flexible than HDPE. The flexible tip portion cap 166 is comprised of the relatively harder HDPE (when compared to LDPE) to provide structural integrity.

FIG. 32B illustrates the rigid portion 141 having a rigid portion proximal end 241 and FIG. 32A shows the second polymer inside layer proximal end 206 being distal of the rigid portion proximal end 241. In some such embodiments, a diameter of the lumen 180 proximal of the second polymer inside layer 204 is greater than the diameter of the lumen defined by the flexible tip portion 160.

FIG. 32B shows first polymer outside layer proximal end 203 and rigid portion proximal end 241 located adjacent hub 132 of introducer 130. In alternative embodiments, first polymer outside layer proximal end 203 and/or rigid portion proximal end 241 can be located inside of or distal of hub 132.

FIG. 33

Figure 33:
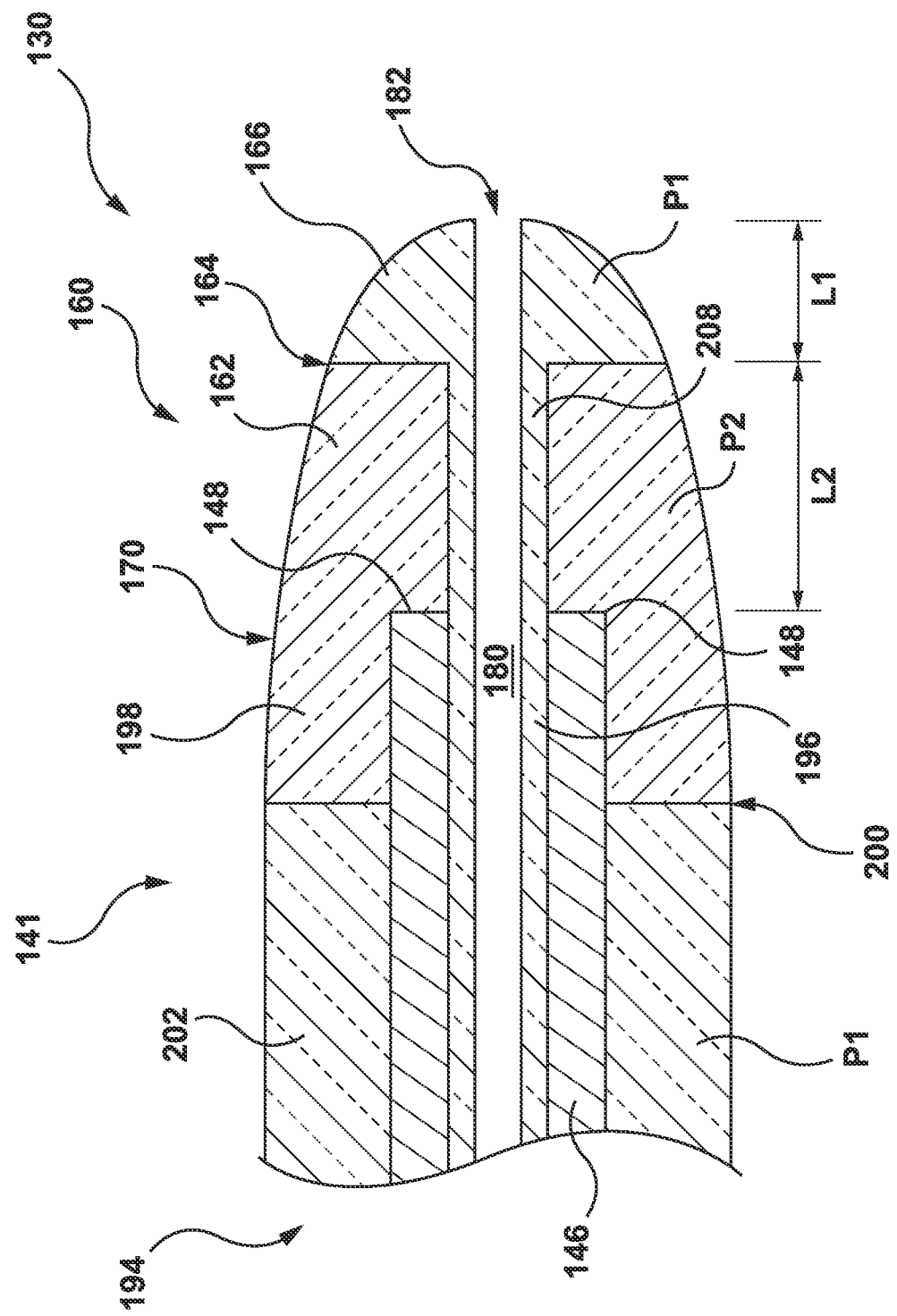
FIG. 33 is a cross-sectional view of another embodiment of the introducer of FIG. 31.

Referring to the surgical introducer 130 of FIG. 33, the second polymer P2 extends proximally from the metal tube distal end 148 on the outside of the metal tube 146 to define a second polymer outside layer 198 which has a second polymer outside layer proximal end 200, and the first polymer P1 extends proximally from the second polymer outside layer proximal end 200 on the outside of the metal tube 146 to define a first polymer outside layer 202.

In the example of surgical introducer 130 of FIG. 33, the second polymer flexible tip segment 162 has a length of length L2, and the second polymer P2 extends proximally from the metal tube distal end 148 on the outside of the metal tube 146 to define a second polymer outside layer 198 which extends longitudinally and proximally from the metal tube distal end 148 for a distance less than length L2.

FIG. 33 illustrates the first polymer P1 extending proximally from the flexible tip portion cap 166 to form a first polymer inside layer 208 whereby the first polymer inside layer 208 defines at least a portion of the lumen 180. In some such embodiments, the rigid portion 141 has a rigid portion proximal end 241 (e.g. FIG. 32B) and the first polymer inside layer 208 extends proximally to the rigid portion proximal end 241 such that the first polymer inside layer 208 defines the lumen 180 from the hub 132 to the distal end opening 182 i.e. the entire lumen 180. In some embodiments, a diameter of the lumen 180 which is defined by the rigid portion 141 is substantially equal to the diameter of the lumen 180 which is defined by the flexible tip portion 160 such that the lumen has a constant diameter FIGS. 34A and 34B Referring to the example of FIG. 34A, surgical introducer 130 comprises an inside layer 196 of polymer on an inside of the metal tube 146 for a distal portion of the metal tube 146. More specifically, the second polymer P2 extends proximally from the metal tube distal end 148 on the inside of the metal tube 146 to define a second polymer inside layer 204 having a second polymer inside layer proximal end 206.

Figure 34B:
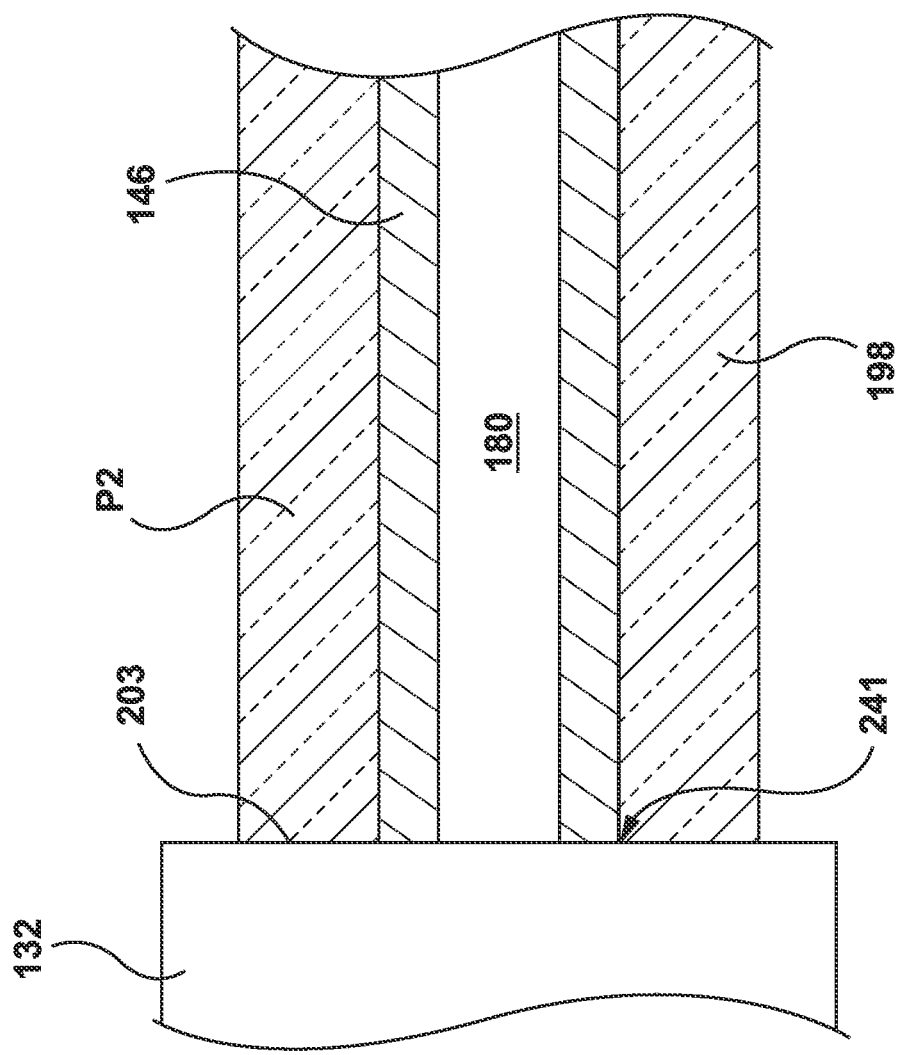

Referring to FIG. 34B, the rigid portion 141 has a rigid portion proximal end 241 and the second polymer outside layer 198 extends proximally to the rigid portion proximal end 241. Rigid portion proximal end 241 and second polymer outside layer proximal end 200 are adjacent hub 132 in the illustrated embodiment. In alternative embodiments, rigid portion proximal end 241 and/or second polymer outside layer proximal end 200 said parts are located inside of or distal of hub 132. In some embodiments, the second polymer inside layer proximal end 206 (FIG. 34A) is distal of the rigid portion proximal end 241 (FIG. 34B).

In the example of FIG. 34A, a diameter of the lumen 180 proximal of the second polymer inside layer 204 is greater than the diameter of the lumen defined by the flexible tip portion 160.

FIG. 35

The embodiment of FIG. 35 includes the first polymer P1 extending proximally from the flexible tip portion cap 166 to form a first polymer inside layer 208 with the first polymer inside layer 208 defining at least a portion of the lumen 180. The first polymer inside layer 208 is inside of metal tube 146 and inside of second polymer flexible tip segment 162. In some such embodiments, the rigid portion 141 has a rigid portion proximal end 241 (e.g. FIG. 34B) and the first polymer inside layer 208 extends to the rigid portion proximal end 241, and thereby defines all of lumen 180. The example of FIG. 35 illustrates a diameter of the lumen 180 which is defined by the rigid portion 141 is substantially equal to the diameter of the lumen 180 which is defined by the flexible tip portion 160 whereby the lumen has a constant diameter.

Figure 20A:
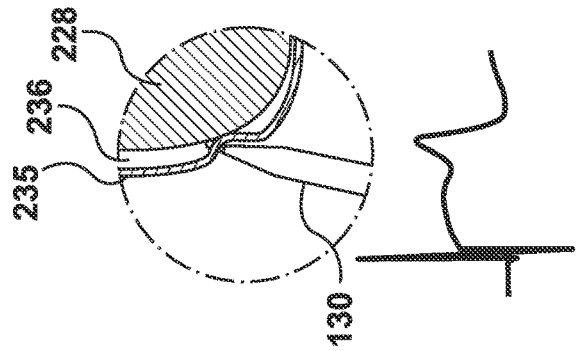
Figure 20B:
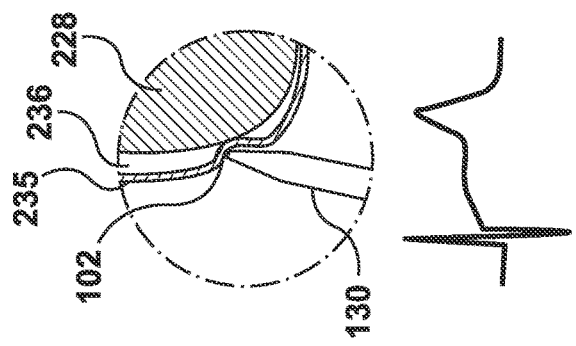
Figure 20C:
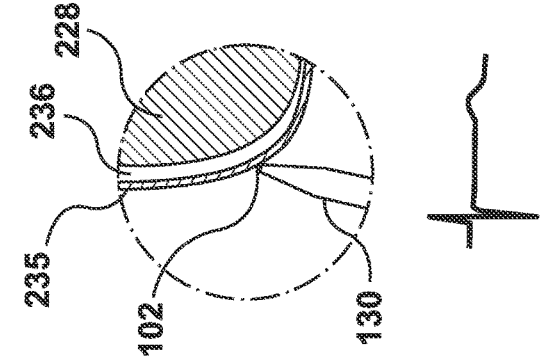
Figure 20D:
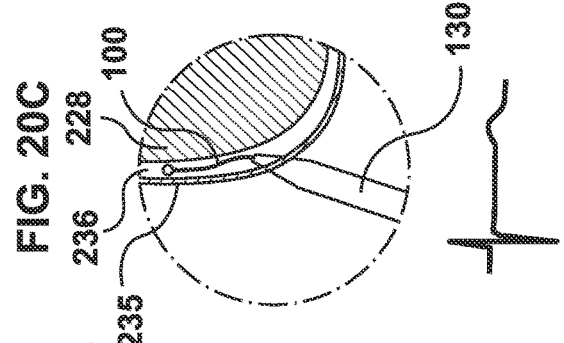
Figure 20E:
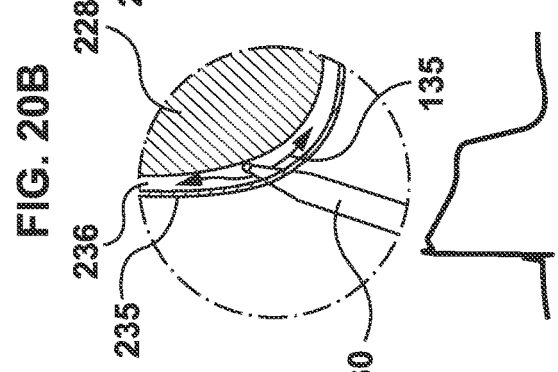
Figure 20F:
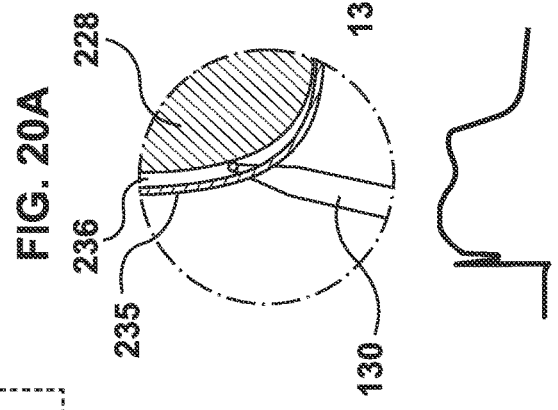

Embodiments of introducer 130 shown in FIGS. 31 to 35 can be used in the method illustrated in FIGS. 20-1 to 20F. The flexible tip portion 160 of introducer 130 can be positioned and orientated against heart 224 in a tangential manner (e.g. FIG. 29B) in the step shown in FIG. 20-1, which is prior to the puncture device contacting the heart.

An alternative embodiment of the invention is a manually reshape-able introducer shaft. This allows the physician to create the desired curve on the shaft of the introducer to facilitate a more curve device insertion trajectory to get underneath the sternum to reach the pericardial sac. This ability reduces the required length of the device in patients with large abdomens or with patients with a more inferior intercostal margin (rib cage).

Figure 8:
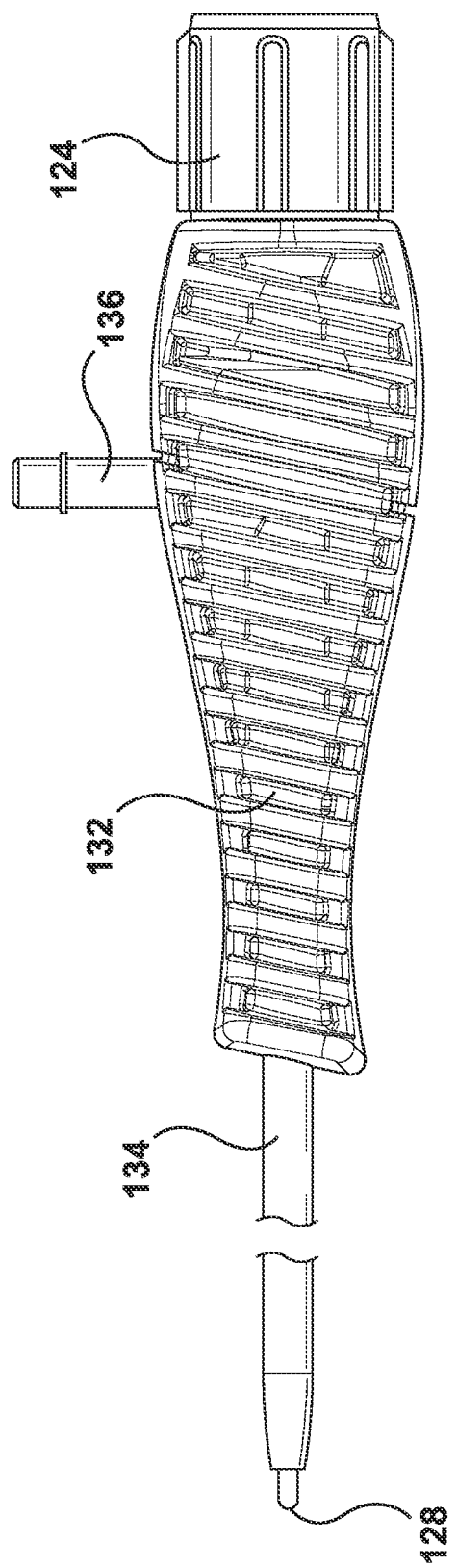
FIG. 8 is a side view of the embodiment of FIG. 7.
Figure 9:
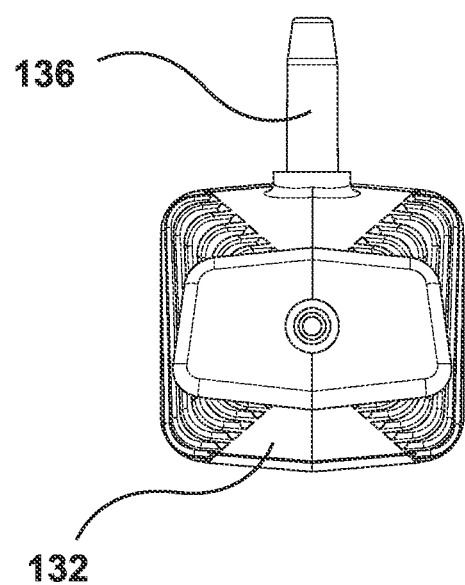
FIG. 9 is an end view of the embodiment of FIG. 7.
Figure 10:
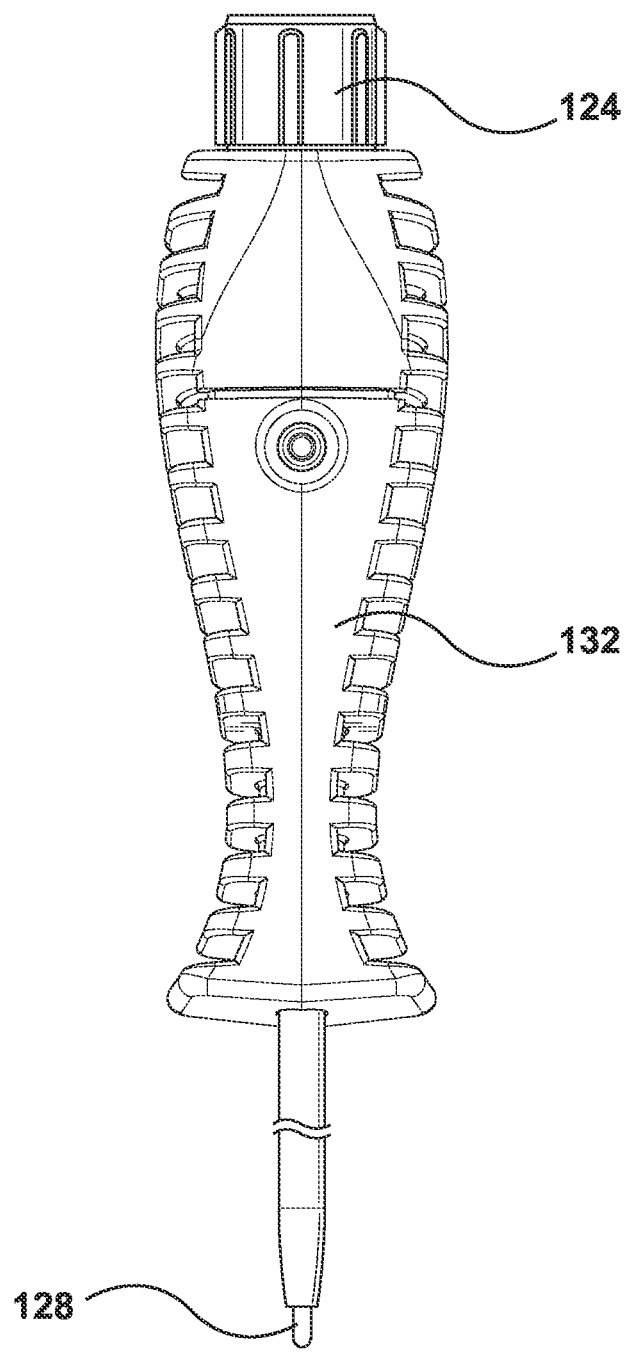
FIG. 10 is a top view of the embodiment of FIG. 7.

FIG. 8 is a side view of the embodiment of FIG. 7 showing introducer shaft 134, hub 132, and male side port 136 of the introducer, and stylet cap 124 and rounded end 128 of the stylet. When a blunt tipped stylet 120 is introduced into introducer 130, the stylet-introducer combination is operable to be advanced through adipose tissue in order to reach the target tissue. FIG. 9 is an end view of the embodiment of FIG. 7 illustrating hub 132 and male side port 136. FIG. 10 is a top view of the embodiment of FIG. 7 which shows stylet cap 124, hub 132, and rounded end 128 of the stylet distal of introducer.

Figure 11:
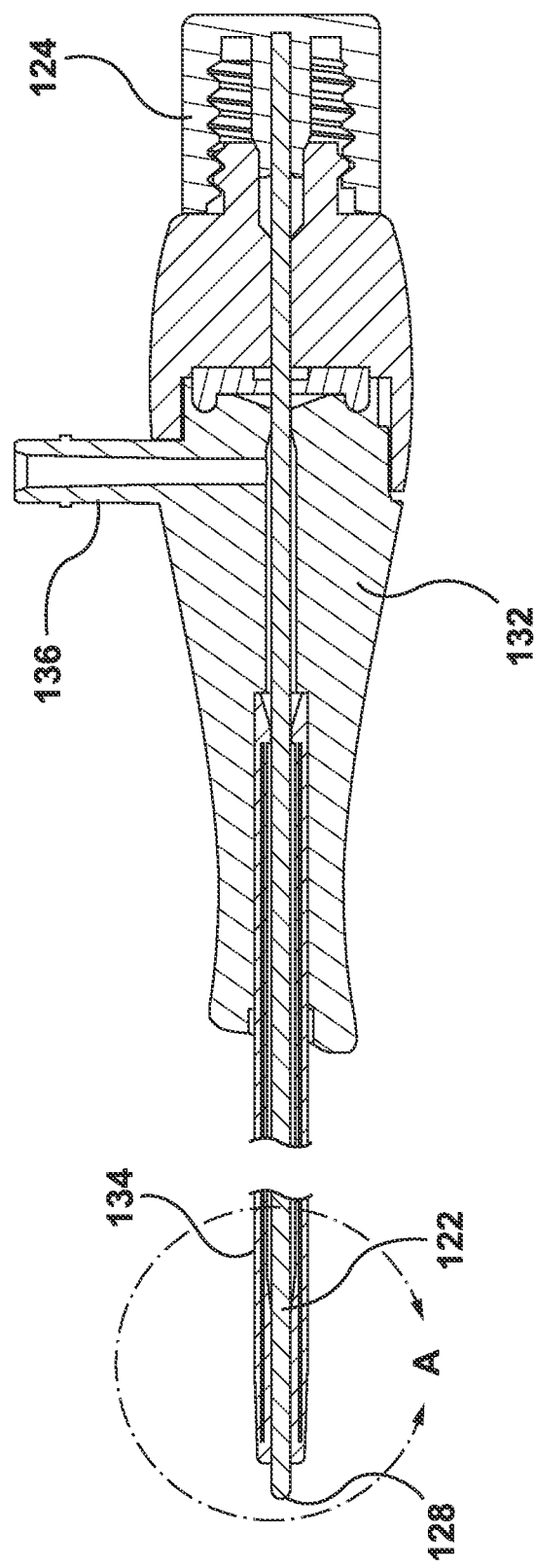
FIG. 11 is a cross sectional view of the embodiment of FIG. 8.
Figure 12:
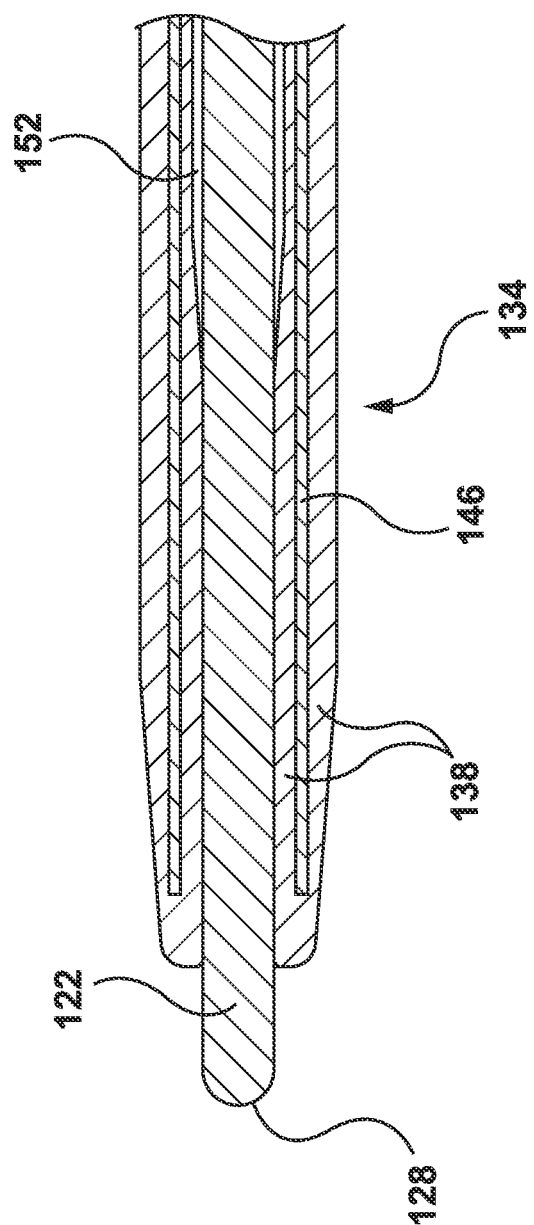
FIG. 12 is an illustration of detail A of FIG. 11.

FIG. 11 is a cross sectional view of the embodiment of FIG. 8. FIG. 11 shows stylet mandrel extending from rounded end 128 to inside of stylet cap 124. To provide for advancing through tissue, rounded end 128 of stylet 120 has a diameter of 0.0375 inches or less, while still being less sharp than a Tuohy needle. FIG. 12 is an illustration of detail A of FIG. 11 which illustrates insulation 138 is on the inside of the lumen defined by introducer shaft 134 as well as on the outside surface of introducer shaft 134. In some embodiments, introducer 130 has an inner diameter >=0.035" (0.89 mm). The shaft of introducer comprises metal tube 146 which is sandwiched (or interposed) between two layers of HDPE (insulation 138) with both ends of the layers of insulation being tipped (i.e. joined together to form a tip) to bond the layers. An introducer 130 with such a configuration can be combined with an elongate puncture device 100 which is a wire is insulated most of its length with the exceptions of the electrode tip and proximal connector to provide apparatus which is effective collecting local EGM. An example is a kit comprising an introducer 130 and an elongate puncture device 100, the elongate puncture device including a distal tip electrode 102 which enables recording epicardial EGM and a shaft of the elongate puncture device is electrically insulated to reduce noise in any collected local EGM, with the introducer comprising an introducer shaft 134 which connected to a hub 132, the introducer shaft comprising a metal tube 146 which is interposed between two layers of electrical insulation 138 with both ends of the two layers being joined together to bond the layers to reduce noise in any EGM collected by the elongate puncture device.

The insulation at distal end of introducer 130 is shaped to form a tip which enables transition through tissue when the intruder is advanced. The length of the introducer shaft 134 is >=5" (12.7 cm). Hub 132 is comprised of plastic and includes a silicone seated valve. FIG. 12 also illustrates the space 152 between stylet mandrel 122 and introducer shaft 134 decreases toward the distal end of introducer shaft 134 i.e. there is a tighter fit between stylet mandrel 122 and introducer shaft 134 at the distal end of introducer shaft 134.

Figure 15:
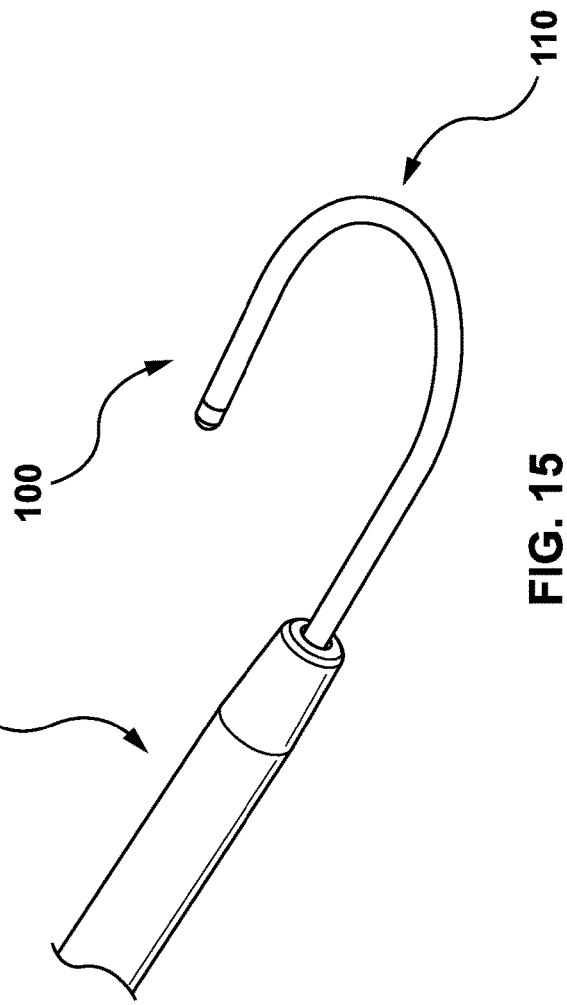
FIG. 15 is an illustration of the embodiment of FIG. 14 with the elongate puncture device extended to form a J-tip.
Figure 14:
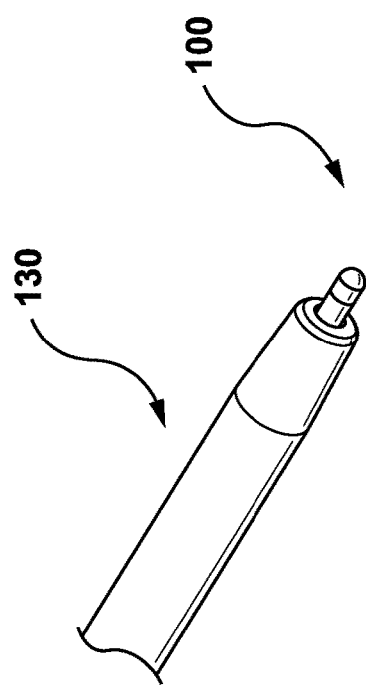
FIG. 14 is an illustration of the distal end of an introducer with a with an elongate puncture device contained therein in accordance with an embodiment of the present invention.

FIG. 13 is an illustration of apparatus of an embodiment which shows the size of the components relative to each other. FIG. 14 illustrates an elongate puncture device 100 extending from introducer 130. Only part of straight portion 112 of the guidewire (FIG. 1) is protruding from the introducer. In some embodiments, the tip of the elongate puncture device 100 is only protruding out 2 mm from the blunt tip of the introducer. This can act as a depth stop in limiting how deep the tip of the elongate puncture device can penetrate the targeted tissue. The tip protrusion length could change depending on support of the tip by the introducer and electrode size. FIG. 15 illustrates a situation in which a distal end portion 110, which has a J-profile, is extended from an introducer 130.

Figure 16:
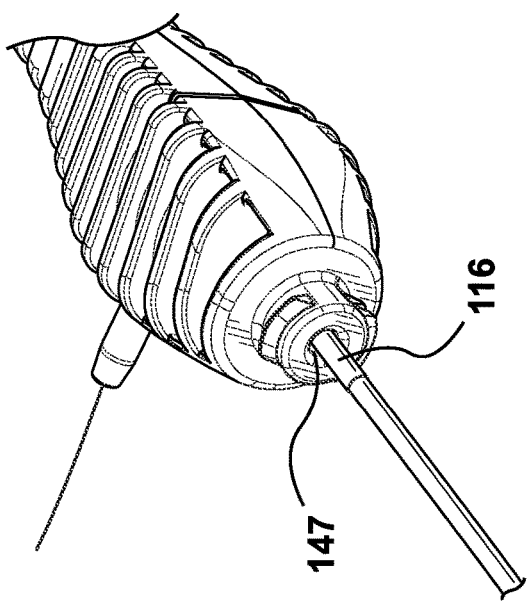
FIG. 16 is an illustration of the proximal end of the hub of FIG. 13 with the elongate puncture device inserted therein.

FIG. 16 shows the proximal end of an introducer hub wherein an elongate puncture device has been inserted such that proximal marker 116 of the guidewire is lined up with the proximal edge of the hub. Proximal marker 116 is visible to a user without the use of an imaging system i.e. it is visible by the naked eye. While typical embodiments of proximal marker 116 are visual markers, in some alternative embodiments, the proximal marker 116 is a tactile marker. In typical embodiments of the apparatus, this positioning of proximal marker 116 indicates the electrode 102 (FIG. 1) is outside the introducer close to the distal end of the introducer i.e. electrode 102 is deployed by positioning it slightly extended out of the distal end of the introducer.

Figure 17:
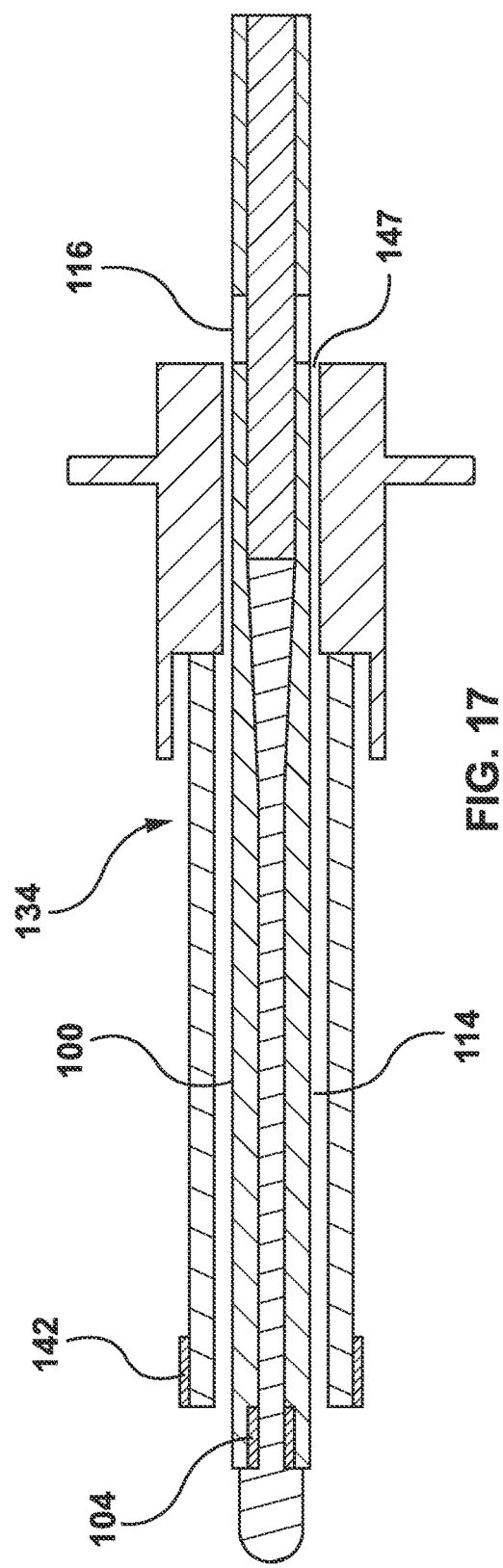
FIG. 17 is a diagrammatic cross-sectional view of an introducer with an elongate puncture device installed therein in accordance with an embodiment of the present invention.

FIG. 17 is a diagrammatic cross-sectional view of an introducer 130 with an elongate puncture device 100 installed therein. In typical embodiments, both the introducer 130 and elongate puncture device 100 include markers for positioning the elongate puncture device 100 relative to introducer 130. In the embodiment of FIG. 17, introducer shaft 134 has a distal marker 142 at its distal end for indicating the position of the distal end of introducer shaft 134 under imaging, and the elongate puncture device has a radiopaque marker 104 at its distal end for indicating the position of the distal end of elongate puncture device under imaging. The position of the distal ends relative to each other can also be determined under imaging. FIG. 17 also shows the elongate puncture device having proximal marker 116 at the proximal end of the introducer hub. In this illustrated embodiment, the tip of the elongate puncture device is extending out of the introducer shaft when proximal marker 116 is positioned at the proximal end of the introducer hub e.g. the line marker on the elongate puncture device helps to inform when the tip is deployed. In alternative embodiments, the tip of the elongate puncture device is line up with the distal tip of the introducer shaft when the proximal marker 116 is positioned at the proximal end of the introducer hub.

Figure 30A:
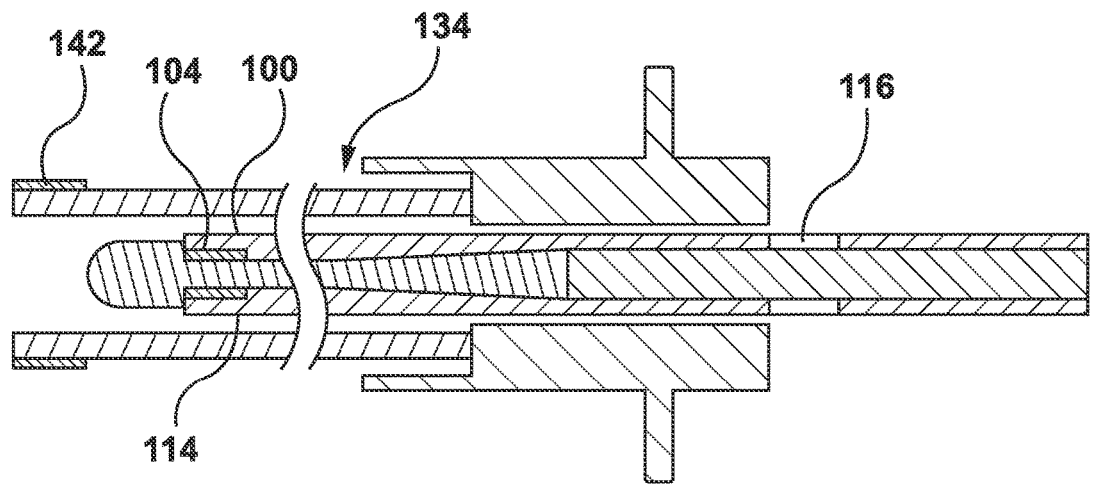
FIGS. 30A to 30C illustrate the steps of a method of advancing an elongate puncture device through an introducer shaft.
Figure 30B:
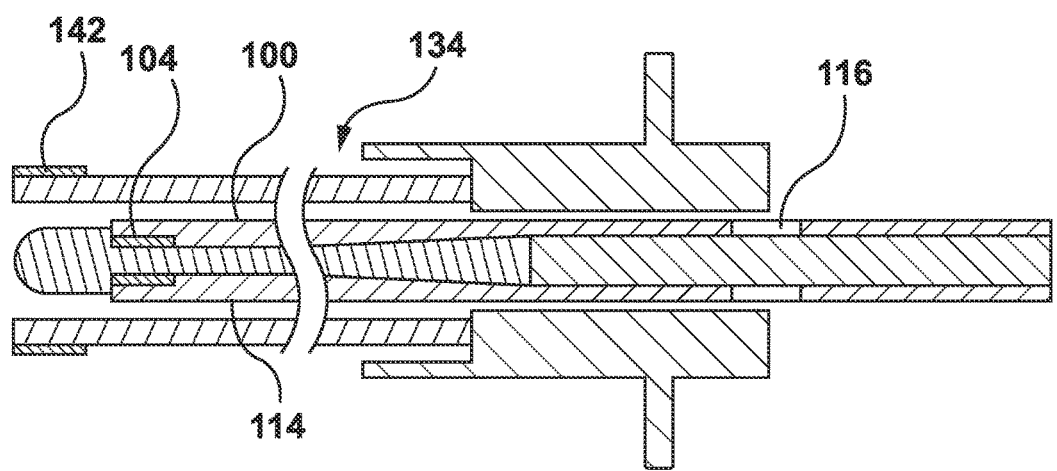
Figure 30C:
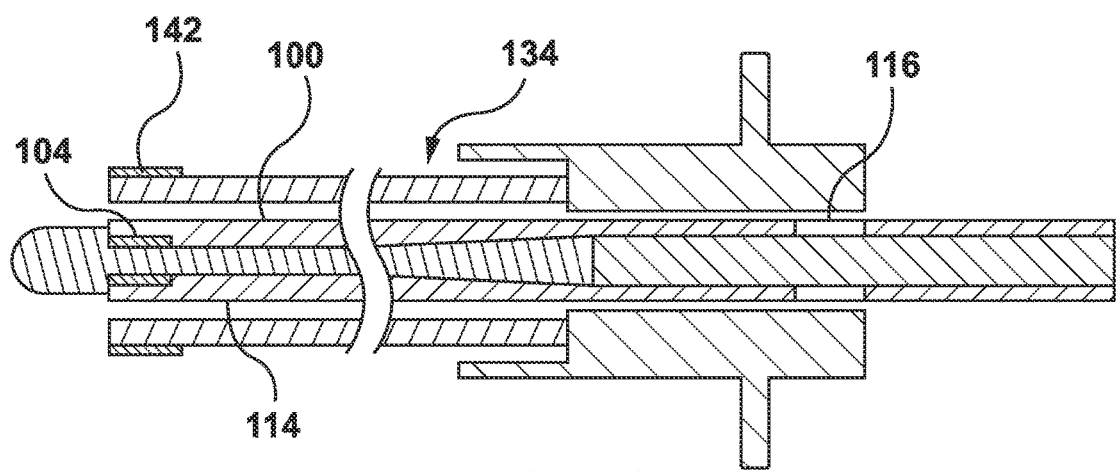

In the embodiment of FIGS. 30A to 30C, introducer shaft 134 has a distal marker 142 at its distal end for indicating the position of the distal end of introducer shaft 134 under imaging, and the elongate puncture device has a radiopaque marker 104 at its distal end for indicating the position of the distal end of elongate puncture device 100 under imaging. FIGS. 30A to 30C show the steps of a method of advancing an elongate puncture device 100 through the introducer shaft 134. FIG. 30A shows the elongate puncture device 100 is positioned to have the distal end of proximal marker 116 at the proximal end of the introducer hub while the tip of the tip of the elongate puncture device still inside of the lumen of the introducer shaft. The elongate puncture device is advanced to the configuration of FIG. 30B wherein the middle of proximal marker 116 at the proximal end of the introducer hub and the tip of the tip of the elongate puncture device lines up with the tip of the introducer shaft 134. The elongate puncture device is further advanced to the configuration of FIG. 30C wherein the proximal end of proximal marker 116 is at the proximal end of the introducer hub and the tip of the elongate puncture device extends beyond the tip of the introducer shaft 134. The configuration on FIG. 30C further includes distal marker 142 of introducer shaft 134 lining up with radiopaque marker 104 at of the distal end of introducer shaft 134, which under imaging, would confirm the relative positioning of the elongate puncture device and introducer.

In some embodiments of the method, the user positions the elongate puncture device relative to the introducer using the proximal marker 116 without using an imaging system such a fluoroscopy in a step that can be called, 'macro-positioning'. Subsequent to the 'macro-positioning', the user turns on an imaging system (e.g. fluoroscopy) for more precise positioning of the elongate puncture device relative to the introducer and the target tissue in a step that can be called micro-positioning. By using the proximal and distal markers, a user can perform the early part of positioning the apparatus without fluoroscopy to thereby reduce the amount of X-rays the user and patient are exposed to when compared to performing the entire procedure under fluoroscopy. In some alternative embodiments of the method, the part of the procedure involved with positioning the elongate puncture device relative to the introducer is performed without any fluoroscopy.

Figure 18:
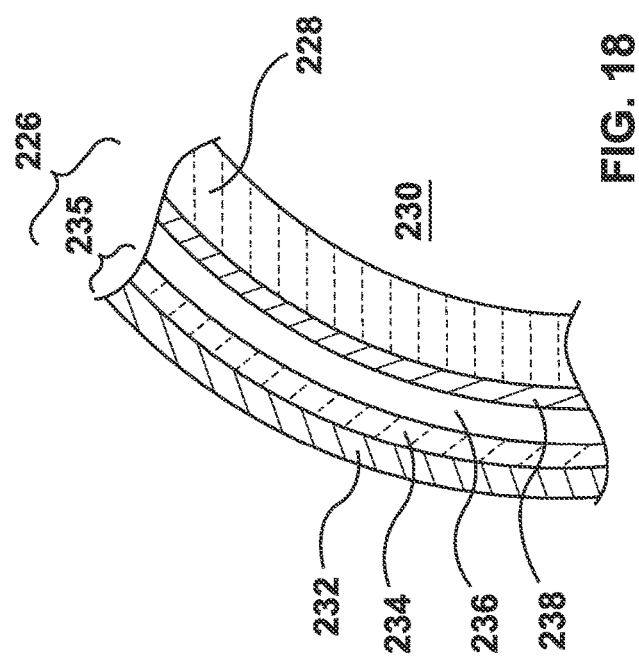
FIG. 18 is an illustration of the layers surrounding a heart.

FIG. 18 is an illustration of the layers surrounding a heart. Ventricle 230 is surrounded by the muscular tissue of the heart, myocardium 228. Pericardium 226 surrounds the myocardium 228 and is comprised of fibrous pericardium 232, parietal layer 234, pericardial cavity 236, and epicardium 238. The pericardial cavity is often referred to as the pericardial space or the space.

Figure 19:
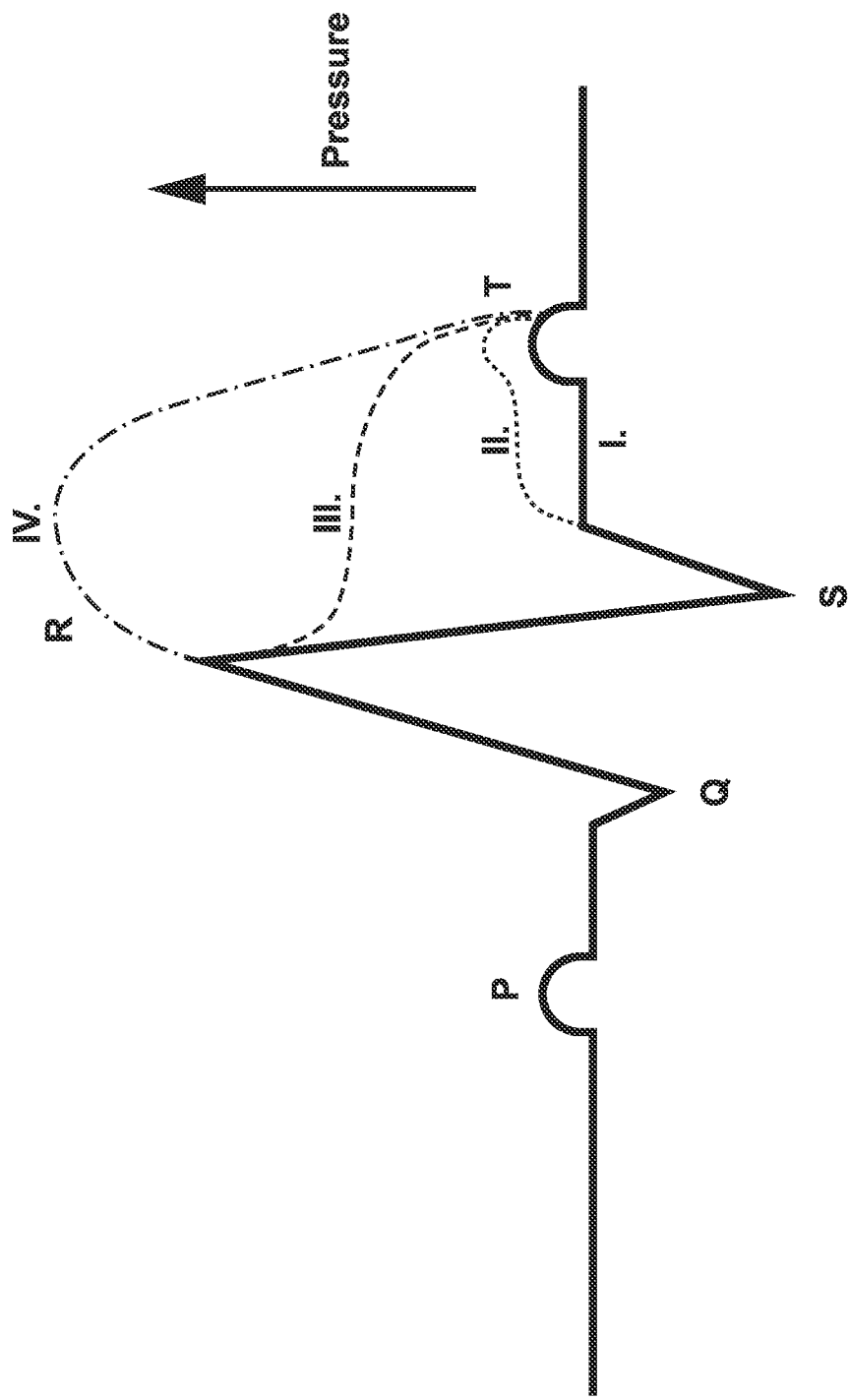
FIG. 19 is an illustration of EGM waves showing a sequence of raised ST segments.

FIG. 19 is an illustration of epicardial EGM waves showing elevated ST segments in response to tenting the pericardium resulting in an ischemic response of the tissue affecting the local epicardial EGM. Such waves can be collected using electrode 102 of an elongate puncture device 100 when the elongate puncture device is advanced and pushed against the pericardium. Line (I) of FIG. 19 is the wave for no tenting (or insignificant pressure) being applied on the pericardium and line (IV) is the wave for very significant tenting of the pericardium. Lines (II) and (III) are for tenting between the amounts of tenting resulting in lines (I) and (IV).

FIG. 20-1, and FIG. 20A to FIG. 20F illustrate an embodiment of a method. The following described method can be performed using the different embodiments of the apparatus previously described. FIG. 20-1 illustrates a sub-xiphoid approach of introducer 130 relative to pericardium 226 and the surrounding anatomy. When a blunt tipped stylet 120 (FIG. 19) is introduced into introducer 130, the stylet-introducer combination is operable to be advanced through adipose tissue in order to reach the target tissue. Typically, stylet 120 is fastened to the proximal end of the hub 132 of introducer 130 (FIG. 11). A physician makes a small nick in the patient's skin to allow the introducer 130 with the protruding stylet tip to pass through the dermal and adipose layers. The blunt tip of stylet 120 provides the necessary cutting action to separate tissue to reach the target. Using a stylet with a blunt tip is advantageous over using stylet with a sharp bevelled tip that will lacerate the tissue as the device traverses through tissue. A blunt tip is also more forgiving if inadvertently advanced too close to the target tissue. It is less likely to puncture the epicardial surface of the heart. Furthermore, other factors being equal, a stylet with a blunt tip provides more tactile feedback than a stylet with a sharp tip. Note that the procedure is done under fluoroscopy.

After the stylet 120 is removed from introducer 130, introducer 130 has a rigid shaft that can support the deployment of an elongate puncture device 100 which is flexible and has a soft tip. The guidewire has a dome tip (electrode dome 103) that can dock with the tissue preventing premature puncture. The physician can optimize their position of the tip of the wire. The introducer has a metal tube 146 (FIG. 12) with a lip that is typically within 0.5 to 2 mm from the tip. The metal tube 146 functions as a radiopaque marker to indicate where the tip of introducer 130 is located. The physician places the tip of the elongate puncture device 100 outside the introducer 130 to ensure proper delivery of RF electrical energy. The physician can advance and retract the tip of the wire under fluoroscopy to gauge how far the wire is sticking out from the tip of the introducer. FIG. 20A illustrates electrode 102 of the elongate puncture device being in contact with the pericardium without any significant force being exerted. The associated EGM, with a low ST segment, is shown below (in the lower part of the figure). FIG. 20B shows the introducer 130 and electrode 102 of the guidewire exerting some force to cause tenting of the pericardium. The wave associated with FIG. 20B is higher than the wave associated with FIG. 20A. In this method, the EGM can be measured while moving devices, and before and after devices are moved.

FIG. 20C illustrates energy being delivered through the electrode to the tissue of the pericardium. The ST segment of the EGM wave shows higher elevation than that of the previous waves. The guidewire has a blunt electrode at the tip to safely dock with tissue and thereby facilitate directly delivering RF energy to the targeted tissue, which the electrode 102 is in contact with. A short pulse (e.g. ⅓ second) of high voltage AC is delivered by the electrode to create a hole in the pericardial sac 235, after which the sac will prolapse over the guidewire tip. The delivery of a short pulse (e.g. ⅓ second) of RF energy aids in limiting depth of puncture. A physician could use a longer pulse but risk the chance of penetrating deep into the myocardial tissue. In alternative embodiments the pulse is shorter or longer depending on power settings and required tissue penetration.

FIG. 20D shows the distal portion of introducer after being advanced into the pericardial cavity 236 and the associated wave, which has an elevated ST segment. Introducer 130 has valve 140 (e.g. a stopcock) attached to it by tubing 144 (FIG. 13) and a valve built into hub 132 (a handle) to allow concurrent delivery of contrast media. This will allow the physician to confirm the tip location of introducer 130 with or without the guidewire in place. The inner diameter of the introducer 130 is large enough to accommodate contrast media flow with a cannulated wire. This configuration of the devices allows the physician to withdraw fluid from the pericardial space. For example, if there is excess fluid or blood, it can be aspirated. The arrows in FIG. 20E represent imaging fluid being injected into pericardial cavity 236. If the imaging of the fluid indicates the fluid is in the pericardial cavity 236, then access to the cavity has been achieved.

FIG. 20F shows a tip the elongate puncture device 100 being advanced into the pericardial cavity 236. The guidewire (elongate puncture device 100) can then be advanced more fully into the space. If the tip of the elongate puncture device continues to move freely after accessing the pericardial space, a physician can confirm access by wrapping the guidewire around the heart at least once (i.e. advancing around the cardiac silhouette) and visualizing under fluoroscopy that the guidewire outlines the cardiac silhouette. The distal 3 cm of the elongate puncture device 100 has a radiopaque coil 106 which increases visibility of the distal end portion 110 under visualization, thereby helping to confirm access to the pericardial space when advancing the tip of the elongate puncture device.

Figure 21A:
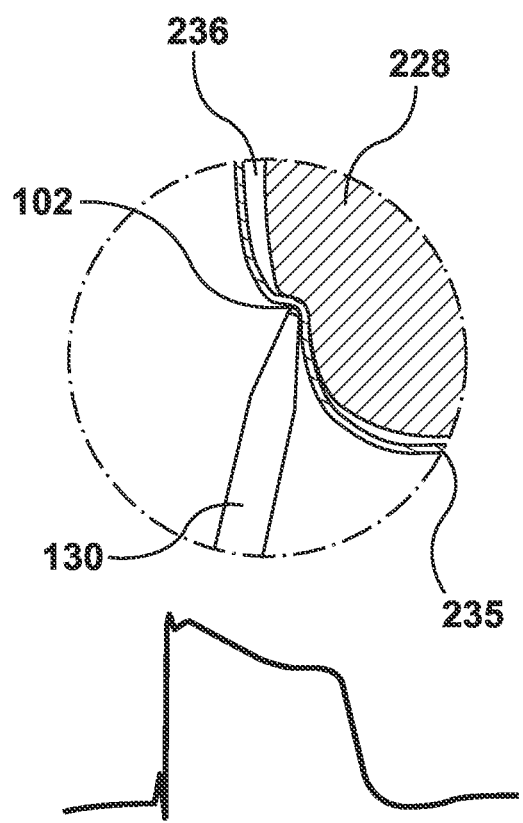
FIGS. 21A and 21B illustrate possible problem scenarios.
Figure 21B:
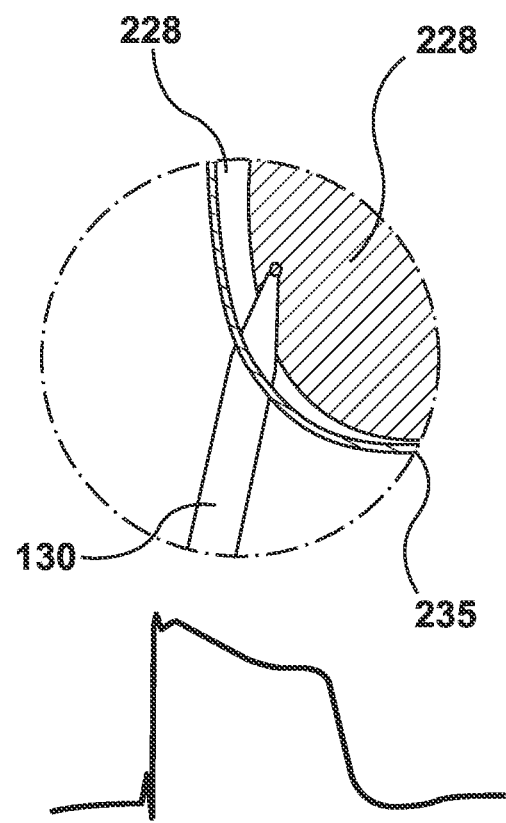

The tip of the wire starting to bunch up when the physician is attempting to advance the elongate puncture device can indicate access to the pericardial cavity 236 has not been achieved. FIG. 21A illustrates the complication scenario in which the epicardium is not punctured and significant tenting occurs. The significant tenting is caused by a significant pressure being applied, resulting in a wave with an elevated ST segment. FIG. 21B illustrates another complication scenario an elongate puncture device passes through the pericardial cavity 236 and into the myocardium 228, resulting a in a wave with an elevated ST segment which is similar to the wave of FIG. 21A.

Elongate puncture device 100 has features facilitating epicardial EGM collection (and non-epicardial EGM collection e.g. EGM collection at the septum of a heart).

Typical embodiments of elongate puncture device 100 comprise a single electrode at the tip of the guidewire which enables recording epicardial EGM from distal tip of the elongate puncture device 100 while tenting tissue. Alternative embodiments of elongate puncture device 100 have multiple electrodes at the tip to collect additional information.

Typical embodiments of elongate puncture device 100 are comprised of material which is electrically conductive to allow for the flow of current.

The electrode 102 is comprised of a material (e.g. Nitinol) which provides for a stable impedance contact with tissue. Impedance depends on the electrode material, tissue, electrode surface area and the temperature. A lower impedance means it less likely for EGM signal to go silent (a DC offset problem). In typical embodiments the electrode is comprised of a solid material. In alternative embodiments, the electrode has a coating of electrically conductive material.

If the electrode surface area is too large, EGM recording resolution will be negatively impacted. An electrode surface area which is too small is susceptible to electrical interference. Some embodiments of the electrode have hemispherical electrode tips (electrode dome 103) with outer diameters between 0.024" (0.62 mm) and 0.035" (0.89 mm). Such embodiments were tested on in vivo porcine study which found that the effects of varying the OD and surface area of the electrode tip (with a CardioLab electrophysiology recording system) showed no observable differences between hemispherical electrode tips with outer diameters between 0.024" (0.62 mm) and 0.035" (0.89 mm). Electrode dome 103 has a dome geometry which ensures uniform contact with tissue at various angles of trajectory. To enable the user to collect epicardial EGM to provide guidewire tip location, on embodiment of the tip electrode has a dome OD >0.027" (0.686 mm) and a wire tip surface area of about 1.8 to about 2.4 mm$^2$ (wherein the dimensions are accurate to one decimal place) such that the electrode is small enough for puncturing tissue while being large enough for effective EGM collection. Further, to create a puncture smaller than a 17Ga Tuohy needle (OD<0.058" or 1.5 mm), some embodiments have a distal tip electrode OD of about 0.0275 inches (0.70 mm).

The shaft of elongate puncture device 100 has features which facilitate collecting an EGM signal. The shaft of elongate puncture device 100 is electrically insulated to reduce noise from the collected local EGM. Also, the inner diameter of introducer 130 and the outer diameter of elongate puncture device 100 enable the introducer and elongate puncture device to fit together with clearance to facilitate delivering contrast agent at the same time as collecting epicardial EGM.

The following method can be performed using the different embodiments of the apparatus previously described. A method which uses the above described devices to puncture a target tissue to gain access to the pericardial cavity 236 comprises the steps of:

(1) Connecting an electrically insulated wire, with one distal pole (e.g. an elongate puncture device 100 which is a RF guidewire), to a recording system that has an electrocardiographic reference to the patient (e.g. EKG pads, subcutaneous reference or intracardiac reference catheter).

(2) Puncturing the patient's skin in a minimally invasive manner via the subxiphoid, parasternal intercostal or apical approach with a rigid introducer and an engaged stylet. A small nick is made in the patient's skin below the xiphoid process to initiate the introduction.

(3) The rigid introducer 130 and stylet 120 are advanced traversing through various dermal layers and toward the pericardial sac of the heart under the guidance of fluoroscopy and tactile feedback to position the tip of the introducer near the pericardial sac. In some embodiments of the method, the stylet is insulated and connected to a recording system to facilitate collecting electrocardiographic information to help in positioning the tips of the devices when approaching the heart (i.e. in large scale positioning).

(4) The stylet 120 is removed, with the blunt radial tip of the introducer docking with the pericardial sac, and replaced with the elongate puncture device 100.

(5) Elongate puncture device 100 is advanced with the introducer 130 contacting the outside of the pericardial sac.

(5a) Local epicardial electrograms, EGMs are recorded from the electrode tip of elongate puncture device 100. As the guidewire travels inside introducer 130 there is little to no signal. Once the tip of elongate puncture device 100 is near or protruding from the tip of introducer 130, the guidewire will start to collect an EGM signal. Under fluoroscopic guidance, the guidewire is advanced until the tip is protruding 2 mm from the tip of the introducer, thereby making contact with the pericardial sac. The tip of elongate puncture device 100 is blunt to prevent lacerating the hearts surface or prematurely puncturing the pericardial sac or myocardial tissue. The blunt tip allows the physician to optimize the location, orientation and angle of approach of the device.

(5b) As the tip of the elongate puncture device contacts the pericardial sac, the amplitude of the waveforms will increase with higher mechanical force (tenting) against the heart due to transient ischemic response of the pericardial sac and epicardial tissue. Note: if the device (electrode 102) is not up against the pericardial sac it will collect far field EGMs or other local EGMs, for example, from the diaphragm.

(5c) Elongate puncture device 100 is docked with the introducer 130, and the elongate puncture device and the introducer are advanced or retracted together to increase or decrease force required for a successful puncture. The local EGM acts as an indirect pressure sensor. The recorded EGM trace will show evidence of an elevated ST segment. The physician can monitor the amount of tenting of the tissue indicated by the amplitude of the ST segment. As part of an interactive approach, a set elevated ST segment is selected which the physician believes to provide adequate tenting to avoid overshoot. The physician may also use tactile feedback when grasping the guidewire when docked against the pericardial sac. Contrast medium can also be injected through the introducer exiting at the tip to confirm adequate tenting of the sac.

(6) Delivering energy to the pericardial sac through the electrode 102 at the tip of elongate puncture device 100. For safety, energy is typically delivered as a pulse (e.g. ⅓ second). Some embodiments include delivering less energy in the pulse by selecting a lower power level or shorter pulse time if a higher pressure level is selected in step (5c). In such embodiments, there is an inverse proportional relationship between the pressure exerted on the sac and the amount of energy delivered in a pulse. In typical embodiments, the physician starts with a low pressure level in the first iteration to avoid overshoot, and the amount of pressure exerted on the pericardial sac is increased with each iteration (while maintaining the same pulse time and energy level) with the physician looking for higher ST elevation to reattempt access.

(6a) Checking if the pericardial sac has been punctured and access to the pericardial cavity has been gained (using previously described techniques). Upon puncture, the pericardial sack will then prolapse over the guidewire tip. If access has not been gained the elongate puncture device is retracted and repositioned on the pericardial sac for another attempt, and the physician returns to step (5c).

(7) Monitoring the electrical activity of the epicardial surface using electrode 102 on the distal tip of elongate puncture device 100 (after RF puncture of the pericardial sac provides access to the pericardial cavity).

(8) Deploying the elongate puncture device 100 further into the pericardial space. Deploying the elongate puncture device 100 further into the pericardial space will relax pressure at the tip and cause a change in the EGM trace. The physician may deliver contrast medium to further confirm access.

Some embodiments include the further step (9) of deploying the guidewire for tracking along the epicardial surface of the heart while collecting local epicardial EGM. The recorded signal can be inputted into EP (electrophysiology) mapping systems for added information.

Elongate puncture device 100 can support a sheath. Typical embodiments include the further step of advancing a sheath and dilator over elongate puncture device 100. Once the sheath tip is positioned appropriately within the pericardial space, the dilator and guidewire are removed. Subsequently, the sheath provides an access portal for advancement and placement for devices such as mapping or ablation catheters to facilitate diagnosis or therapy of a variety of arrhythmias. Some such embodiments of the method include the use a steerable sheath.

Also, some embodiments use a system including an amplifier with the ability to amplify voltages and measure impedance from an electrode across a range of anatomically relevant frequencies (from about 10 kHz to about 80 kHz).

While not considered as a step in the prescribed method, it is possible for the elongate puncture device to be embedded into the epicardium or ventricle after RF puncture. In these situations, the amplitude of the electrical activity (ST segment) decreases, providing feedback to the user that the guidewire should be retracted and RF puncture could be reattempted. These situations can also be confirmed with fluoroscopy.

Some embodiments of the present invention comprise a method of confirming a position of a tip of a puncture device relative to a target tissue which includes using an elongate puncture device having a tip electrode that is configured for collecting EGMs and for delivering energy for puncturing tissue. The method comprises a step of collecting EGMs with the tip electrode to indirectly measure and monitor a pressure applied against the target tissue by the tip electrode of the elongate puncture device. Other embodiments of the present invention comprise a method of puncturing a target tissue which includes using an elongate puncture device having a tip electrode that is configured for collecting EGMs and for delivering energy for puncturing the target tissue, the method comprising collecting EGMs to indirectly measure and monitor a pressure applied against the target tissue by the elongate puncture device, thereby confirming a position of the tip electrode of the elongate puncture device relative to the target tissue.

In a first broad aspect, embodiments of the present invention include an introducer for use with an elongate puncture device, with the surgical introducer comprising an introducer shaft having a rigid portion and a flexible tip portion. The rigid portion has a rigid portion distal end, with a metal tube extending to the rigid portion distal end. The metal tube has a metal tube distal end. The flexible tip portion is distal of the metal tube distal end, with the flexible tip portion including a first polymer and a second polymer, and the second polymer being more flexible than the first polymer. The second polymer extends distally from the metal tube distal end to define a second polymer flexible tip segment having a second polymer flexible tip segment end. The first polymer extends distally from the second polymer flexible tip segment end to define a flexible tip portion cap. The rigid portion and the flexible tip portion define a lumen, and the flexible tip portion cap defines a distal end opening which is in fluid communication with the lumen.

The embodiments of the invention described above are intended to be exemplary only. The scope of the invention is therefore intended to be limited solely by the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

EXAMPLES

1. A method of confirming a position of a tip of a puncture device relative to a target tissue includes using an elongate puncture device having a tip electrode which is configured for collecting EGMs and for delivering energy for puncturing tissue, and comprises a step of collecting EGMs with the tip electrode to indirectly measure and monitor a pressure applied against the target tissue by the tip electrode of the elongate puncture device.
2. The method of example 1, wherein the target tissue is a pericardium.
3. The method of example 1, wherein the target tissue is a septum of a heart.
4. The method of example 3, wherein the target tissue is an atrial septum.
5. The method of any one of examples 1 to 5, wherein the elongate puncture device delivers radiofrequency energy.
6. The method of example 5, wherein the elongate puncture device is a radiofrequency stylet, trocar or guidewire.
7. The method of example 1, wherein the EGMs are collected from a pericardium.
8. The method of example 1, wherein the EGMs are collected from a septum of a heart.
9. The method of example 1 or 7, wherein the elongate puncture device applies pressure against pericardial tissue.
10. The method of example 1 or 8, wherein the elongate puncture device applies pressure against a septum of a heart.
11. A method of puncturing a target tissue includes using an elongate puncture device having a tip electrode which is configured for collecting EGMs and for delivering energy for puncturing the target tissue, the method comprising collecting EGMs to indirectly measure and monitor a pressure applied against the target tissue by the elongate puncture device, thereby confirming a position of the tip electrode of the elongate puncture device relative to the target tissue.
12. The method of example 11, wherein the target tissue is a pericardium.
13. The method of example 11, wherein the target tissue is a septum of a heart.
14. The method of example 13, wherein the target tissue is an atrial septum.
15. The method of example 11, wherein the elongate puncture device delivers radiofrequency energy.
16. The method of any one of examples 11 to 15, wherein the elongate puncture device is a radiofrequency guidewire.
17. The method of example 11, wherein EGMs are collected from a pericardium.
18. The method of example 11, wherein EGMs are collected from a septum of a heart.
19. The method of example 11 or 17, wherein the elongate puncture device applies pressure against pericardial tissue.
20. The method of example 11 or 18, wherein the elongate puncture device applies pressure against a septum of a heart.
21. A method of gaining access to a pericardial cavity comprising the steps of:
    (a) introducing a blunt tipped stylet into an introducer;
    (b) advancing the blunt tipped stylet and the introducer, in combination, through adipose tissue towards a tissue of the pericardium;
    (c) removing the stylet from the introducer;
    (d) installing an elongate puncture device, which is flexible, in the introducer;
    (e) advancing the tip of the elongate puncture device to be distal of the introducer under fluoroscopy whereby an electrode of the elongate puncture device is in contact with a pericardium without any significant force being exerted;
    (f) monitoring an EGM based on the electrode of the elongate puncture device which is in contact with the pericardium to confirm there is a low ST segment;
    (g) exerting force with the introducer and the electrode of the guidewire to tent the pericardium;
    (h) monitoring the EGM to confirm the wave is higher than the wave of step (f);
    (i) delivered energy through the electrode to the tissue of the pericardium; and
    (j) monitoring the EGM the ST segment is higher than the waves of steps (f) and (h).
22. The method of example 21, wherein step (i) includes delivering a short pulse of high voltage AC.
23. The method of example 22, wherein the short pulse is ⅓ second.
24. The method of example 21, further comprising a step (k) of advancing the distal portion of the introducer into the pericardial cavity and monitoring the EGM.
25. The method of example 21, wherein steps (e) and (f) are performed simultaneously.
26. The method of example 21, wherein steps (g) and (h) are performed simultaneously.
27. The method of example 21, wherein steps (i) and (j) are performed simultaneously.
28. The method of example 24, further comprising a step (l) of delivering a contrast media.
29. The method of example 24, further comprising a step (m) of withdrawing fluid from the pericardial space.
30. The method of example 24, further comprising a step (n) of advancing a tip of the elongate puncture device into the pericardial cavity.
31. The method of example 24, further comprising a step (n) of advancing the elongate puncture device into the pericardial cavity.

32. The method of example 31, further comprising a step (o) of confirming access by wrapping the guidewire around the heart at least once and visualizing under fluoroscopy.
33. A method of puncturing a target tissue to gain access to the pericardial cavity comprises the steps of:
  (1) connecting an electrically insulated wire having one distal pole to a recording system that has an electrocardiographic reference to the patient;
  (2) puncturing the patient's skin via the subxiphoid, parasternal intercostal or apical approach with a rigid introducer and an engaged stylet;
  (3) advancing the rigid introducer and the stylet through various dermal layers and toward the pericardial sac of the heart under the guidance of fluoroscopy and tactile feedback to position the tip of the introducer near the pericardial sac;
  (4) removing the stylet while a blunt radial tip of the introducer is docking with the pericardial sac, and installing the elongate puncture device in the introducer;
  (5) advancing the elongate puncture device while the introducer is contacting the outside of the pericardial sac; and
  (6) delivering energy to the pericardial sac through the electrode at the tip of Elongate puncture device.
34. The method of example 33, wherein step (5) includes recording local epicardial EGMs from the electrode tip of the elongate puncture device.
35. The method of example 34, wherein step (5) further comprises monitoring the EGM to confirm the amplitude of the waveforms increases with higher mechanical force against the heart.
36. The method of example 33, wherein step (6) comprises the energy being delivered as at least one pulse.
37. The method of example 33, wherein step (6) comprises the energy being delivered as a series of pulses, starting with a low pressure level against the pericardial sac in the first iteration to avoid overshoot, and the amount of pressure exerted on the pericardial sac is increased with each iteration while maintaining the same pulse time and energy level.
38. The method of example 33, wherein step (6) comprises checking if the pericardial sac has been punctured and access to the pericardial cavity has been gained.
39. The method of example 33, further comprising a step (7) of monitoring the electrical activity of the epicardial surface using the electrode on the distal tip of the elongate puncture device (after RF puncture of the pericardial sac provides access to the pericardial cavity).
40. The method of example 39, further comprising a step (8) of deploying the elongate puncture device further into the pericardial space to relax pressure at the tip and cause a change in the EGM trace.
41. The method of example 40, further comprising a step (9) of deploying the guidewire for tracking along the epicardial surface of the heart while collecting local epicardial EGM.
42. The method of example 40, further comprising the step of advancing a sheath and dilator over the elongate puncture device.
43. A method of confirming a position of a tip of an elongate puncture device relative to an introducer wherein the elongate puncture device has a proximal marker which is visible to a naked eye and a distal tip marker which is visible under an imaging system, and the introducer has distal end marker which is visible under the imaging system, the method including the steps of: (1) positioning the elongate puncture device relative to a proximal end of the introducer using the proximal marker without an imaging system; (2) turning on the imaging system; and (3) positioning a distal tip of the elongate puncture device relative to an end of introducer by viewing the distal tip marker and distal end marker using the imaging system.
44. The method of example 43, wherein the imaging system is a fluoroscopy system and the distal tip marker and distal end marker are visible under fluoroscopy.
45. An elongate puncture device comprising: a mandrel which is electrically conductive and covered by a clear layer of insulation, the clear layer stopping short of a distal end of the mandrel such that the distal end of the mandrel is electrically exposed to define a distal tip electrode, a portion of the mandrel being surrounded by a visible marker, the visible marker being covered by the clear layer, wherein the portions of the elongate puncture device at and adjacent the visible marker have a constant outer diameter.
46. The elongate puncture device of example 45, wherein the mandrel is surrounded by an oxide coating which is covered by the clear layer of insulation, wherein for at least one portion of the mandrel the oxide coating has been removed such that said at least one portion defines at least one visible marker.
47. The elongate puncture device of example 46, wherein the at least one visible marker comprises at least one portion of the mandrel wherein the oxide coating is in contact with the mandrel.
48. The elongate puncture device of example 45, wherein the visible marker may be a proximal marker, an intermediate marker, or a distal marker.
49. The elongate puncture device of example 45, wherein the clear layer comprises a heat-shrink layer.
50. The elongate puncture device of example 47, wherein the heat-shrink layer comprises a polytetrafluoroethylene material.
51. The elongate puncture device of example 45, wherein the mandrel is comprised of a nitinol.
52. The elongate puncture device of example 45, wherein the mandrel is comprised of a stainless steel.
53. The elongate puncture device of example 46, wherein the oxide coating is comprised of a layer of titanium dioxide.
54. The elongate puncture device of any one of examples 45 to 53, wherein the elongate puncture device is flexible.
55. The elongate puncture device of any one of examples 45 to 53, wherein the mandrel is electrically conductive, and a proximal end portion of the mandrel is uninsulated and operable for connecting to a power supply such that the distal tip electrode is in electrical communication with the power supply, and energy can be delivered through the distal tip electrode to tissue, and the distal tip electrode enables recording epicardial EGM.
56. The elongate puncture device of example 55, wherein a shaft of the elongate puncture device is electrically insulated to reduce noise from any collected local EGM.
57. The elongate puncture device of any one of examples 45 to 53, wherein the distal tip electrode has a hemispherical dome with an outer diameter >0.027" (0.686 mm) and a surface area of about 1.8 to about 2.4 mm2.
58. The elongate puncture device of any one of examples 45 to 53, further comprising a distal end portion which has a J-profile.
59. The elongate puncture device of example 58, further comprising a radiopaque coil which extends around a curve of the distal end portion which has a J-profile.
60. The elongate puncture device of example 59, wherein an end of the radiopaque coil can be used as a distal tip marker.
61. The elongate puncture device of example 59, wherein the radiopaque coil has echogenic properties when using ultrasound to enable visualization of the guidewire tip.
62. An introducer for use with an elongate puncture device, the introducer comprising an introducer shaft connected to a hub, the introducer shaft comprising a metal tube which is interposed between two layers of insulation with both ends of the two layers being joined together to bond the layers.
63. The introducer of example 62, wherein the two layers of insulation are comprised of high-density polyethylene.
64. The introducer of example 62 or 63, wherein the hub further comprises a male side port for connecting to tubing and a receiving opening for receiving a stylet or a wire whereby the hub is operable to be simultaneously attached to source of fluid while a stylet or a wire is inserted into the hub.
65. A kit comprising an introducer and an elongate puncture device, the elongate puncture device including a distal tip electrode which enables recording epicardial EGM and a shaft of the elongate puncture device is electrically insulated to reduce noise in any collected local EGM; and
the introducer comprising an introducer shaft which connected to a hub, the introducer shaft comprising a metal tube which is interposed between two layers of electrical insulation with both ends of the two layers being joined together to bond the layers to reduce noise in any EGM collected by the elongate puncture device.
66. The kit of example 65, wherein the introducer and the elongate puncture device are configured such that the introducer has the ability to deliver and withdraw fluid while the elongate puncture device is inserted therethrough.
67. The kit of example 66, wherein the radial gap between an inner diameter of a tip of the introducer and outer diameter of the elongate puncture device is >0.025 mm (0.001").
68. The kit of example 67, wherein the kit is operable to provide contrast flow >15 ml/min at 69 Kilo Pascal (10 PSI).
69. The kit of example 67, wherein the inner diameter of a tip of the introducer is 0.978 mm (0.0385 inches)+/−0.013 mm (0.0005 inches), and the maximum outer diameter of the elongate puncture device is 0.889 mm (0.0350 inches)+/−0.013 mm (0.0005 inches), whereby the minimum gap with this geometry is 0.032 mm (0.00125").
70. The kit of any one of examples 65 to 69, further comprising a stylet wherein a cross section of the stylet varies along the length of the stylet, tapering down towards a distal tip of the stylet to allow a flow of a fluid through a tip of the introducer when the stylet is installed.
71. The kit of any one of examples 65 to 69, further comprising a stylet wherein the stylet is electrically insulated and operable to be connected to a recording system to facilitate collecting EGM information to help in positioning a tip of the introducer when approaching the heart.
72. The kit of any one of examples 65 to 69, further comprising markers for positioning the elongate puncture device relative to the introducer wherein the elongate puncture device has a proximal marker which is visible to a naked eye and a distal tip marker which is visible under an imaging system, and the introducer has distal end marker which is visible under the imaging system.
73. The kit of example 72, wherein the distal tip marker and distal end marker are visible under fluoroscopy.
74. The kit of example 72, wherein a tip of the elongate puncture device extends distal of a shaft of the introducer shaft when the proximal marker of the elongate puncture device is positioned at a proximal end of a hub of the introducer.
75. The kit of example 72, wherein a tip of the elongate puncture device lines up with a distal end of a shaft of the introducer shaft when the proximal marker of the elongate puncture device is positioned at a proximal end of a hub of the introducer.
76. The method of any one of examples 1 to 5, 11 to 15, 21, 33, and 43, wherein the elongate puncture device comprises a radiofrequency guidewire.
77. The elongate puncture device of any one of examples 45 to 53, wherein the elongate puncture device comprises a radiofrequency guidewire.
78. The kit of any one of examples 65 to 69, wherein the elongate puncture device comprises a radiofrequency guidewire.

We claim:
1. A surgical introducer comprising:
an introducer shaft having a rigid portion and a flexible tip portion;
the rigid portion having a rigid portion distal end, a metal tube extending to the rigid portion distal end, and the metal tube having a metal tube distal end; and
the flexible tip portion being distal of the metal tube distal end, the flexible tip portion including a first polymer and a second polymer, the second polymer being more flexible than the first polymer,
the second polymer longitudinally abutted against and extending distally from the metal tube distal end to define a second polymer flexible tip segment having a second polymer flexible tip segment end,
the first polymer longitudinally abutted against and extending distally from the second polymer flexible tip segment end to define a flexible tip portion cap,
the rigid portion and the flexible tip portion defining a lumen,
and the flexible tip portion cap defining a distal end opening which is in fluid communication with the lumen.
2. The surgical introducer of claim 1, wherein the distal end opening is forward facing.
3. The surgical introducer of claim 1, further comprising an outside layer of a polymer on an outside of the metal tube.
4. The surgical introducer of claim 1, further comprising an inside layer of polymer on an inside of the metal tube for at least a distal portion of the metal tube.
5. The surgical introducer of claim 1, wherein the second polymer flexible tip segment has a length of length L2 and the flexible tip portion cap has a length of length L1, and length L2 is greater than length L1.

6. The surgical introducer of claim 1, wherein the flexible tip portion has a length of about 1 to 3 cm.

7. The surgical introducer of claim 1, wherein the flexible tip portion has a length of 2 to 3 cm.

8. The surgical introducer of claim 1, wherein the first polymer is HDPE.

9. The surgical introducer of claim 1, wherein the second polymer is LDPE.

10. The surgical introducer of claim 1, wherein the metal tube is steel.

11. The surgical introducer of claim 1, further comprising the second polymer extending proximally from the metal tube distal end on an outside of the metal tube.

12. The surgical introducer of claim 11, wherein the second polymer defines a second polymer outside layer which has a second polymer outside layer proximal end, and the first polymer extends proximally from the second polymer outside layer proximal end on an outside of the metal tube to define a first polymer outside layer.

13. The surgical introducer of claim 11, wherein the second polymer flexible tip segment has a second polymer flexible tip segment length of length L2 and the second polymer extends proximally from the metal tube distal end on the outside of the metal tube to define a second polymer outside layer which extends longitudinally and proximally from the metal tube distal end for a distance less than length L2.

14. The surgical introducer of claim 13, wherein the rigid portion has a rigid portion proximal end and the second polymer outside layer extends proximally to the rigid portion proximal end.

15. The surgical introducer of claim 1, further comprising the second polymer extending proximally from the metal tube distal end on the inside of the metal tube to define a second polymer inside layer having a second polymer inside layer proximal end.

16. The surgical introducer of claim 15, wherein the rigid portion has a rigid portion proximal end and the second polymer inside layer proximal end is distal of the rigid portion proximal end.

17. The surgical introducer of claim 16, wherein a diameter of the lumen proximal of the second polymer inside layer is greater than the diameter of the lumen defined by the flexible tip portion.

18. The surgical introducer of claim 1, further comprising the first polymer extending proximally from the flexible tip portion cap to form a first polymer inside layer, the first polymer inside layer defining at least a portion of the lumen.

19. The surgical introducer of claim 18, wherein the rigid portion has a rigid portion proximal end and the first polymer inside layer extends proximally to the rigid portion proximal end.

20. The surgical introducer of claim 19, wherein a diameter of the lumen which is defined by the rigid portion is substantially equal to the diameter of the lumen which is defined by the flexible tip portion.

* * * * *